US008580547B2

(12) United States Patent
Weichel et al.

(10) Patent No.: US 8,580,547 B2
(45) Date of Patent: Nov. 12, 2013

(54) VARIANTS OF PQQ-DEPENDENT GLUCOSE DEHYDROGENASE HAVING IMPROVED SUBSTRATE SPECIFICITY

(75) Inventors: Walter Weichel, Odenthal (DE); Volker Möhrle, Köln (DE); Markus Schindler, Emden (DE); Rainhard Koch, Kleinmachnow (DE); Rolandas Meskys, Vilnius (LT)

(73) Assignee: Bayer Intellectual Property GmbH, Monheim (DE)

( * ) Notice: Subject to any disclaimer, the term of this patent is extended or adjusted under 35 U.S.C. 154(b) by 231 days.

(21) Appl. No.: 12/999,465

(22) PCT Filed: Jun. 17, 2009

(86) PCT No.: PCT/EP2009/004350
§ 371 (c)(1),
(2), (4) Date: Apr. 14, 2011

(87) PCT Pub. No.: WO2009/156083
PCT Pub. Date: Dec. 30, 2009

(65) Prior Publication Data
US 2011/0236920 A1 Sep. 29, 2011

(30) Foreign Application Priority Data
Jun. 26, 2008 (DE) .......................... 10 2008 030 435

(51) Int. Cl.
*C12Q 1/32* (2006.01)
*C12N 9/00* (2006.01)
*C12N 9/04* (2006.01)
*C12N 1/20* (2006.01)
*C07H 21/04* (2006.01)

(52) U.S. Cl.
USPC .......... 435/190; 435/26; 435/183; 435/252.3; 435/320.1; 536/23.2

(58) Field of Classification Search
None
See application file for complete search history.

(56) References Cited

U.S. PATENT DOCUMENTS 7,132,270 B2   11/2006 Kratzsch et al.

FOREIGN PATENT DOCUMENTS

| EP | 1146332 A1 | 10/2001 |
| EP | 1367120 A2 | 12/2003 |
| EP | 1666586 A1 | 6/2006 |
| WO | 2006 085509 A | 8/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Igarashi, S; Engineering PQQ glucose dehydrogenase with improved substrate specify . . . , Biomolecular Engineering, 2004, vol. 21, pp. 81-89.
Sode K. et al: Improved Substrate Specificity and Dynamic Range for Glucose Meausurement of *Eschericha coli* PQQ Glucose Dehydrogenase by Site Directed Mutagenesis, Biotechnology Letters, Kew, Surrey, GB, Bd. 19, Nr. 11, Nov. 1997, pp. 1073-1077, ISSN 0141-5492.
Vadgama, J. Med.Eng Technol. 5 [6], 293-298 (1981).
Pauly and G. Pfleiderer, Hoppe Seylers. Z. Physiol Chem. 356 [10], 1613-1623 (1975).
Cleton-Jansen et al., J. Bacteriol. 170 [5], 2121-2125 (1988).
Cleton-Jansen et al., Mol. Gen. Genet. 217 [2-3], 430-436 (1989).
Schleis, Pharmacotherapy 27 [9], 1313-1321 (2007).
Kojima K. et al., Biotechnology Letters 22, 1343-1347 (2000).
Bouvet P.J. and O. M. Bouvet, Res. Microbiol. 140 [8], 531-540 (1989).
Oubrie et al., J. Mol. Biol. 289 [2], 319-333 (1999).
Oubrie et al., EMBO J. 18 [19], 5187-5194 (1999).
Sambrook, J. and Russel, D.W.; Molecular Cloning—A Laboratory Manual; vol. 1; 3rd edition, CSHL Press 2001.
Atkins, Physical Chemistry, W. H. Freeman & Co; 7th edition, 2002, pp. 862-871.
Chua and Tan, Clin. Chem. 24 [1], 150-152 (1978).

* cited by examiner

*Primary Examiner* — Christian Fronda
(74) *Attorney, Agent, or Firm* — Norris McLaughlin & Marcus, P.A.

(57) ABSTRACT

The invention relates to novel PQQ-dependent soluble glucose dehydrogenases (sPQQGDH) which have an increased substrate specificity compared with the wild type, and also to methods for production and identification thereof.

8 Claims, 7 Drawing Sheets

Figure 1:
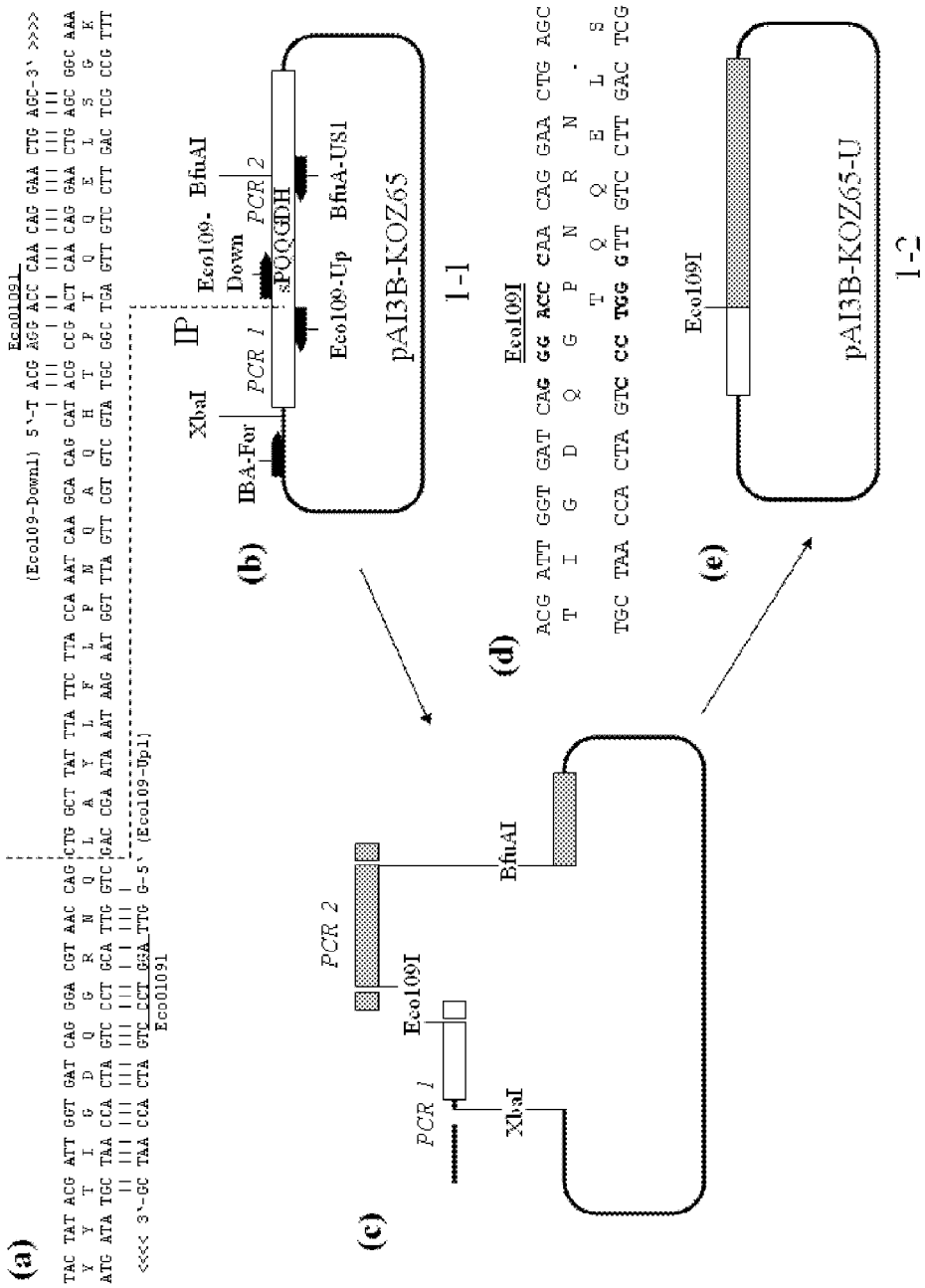

VARIANTS OF PQQ-DEPENDENT GLUCOSE DEHYDROGENASE HAVING IMPROVED SUBSTRATE SPECIFICITY

This application is a 371 of PCT/EP2009/004350, filed Jun. 17, 2009, which claims foreign priority benefit under 35 U.S.C. §119 of the German Patent Application No. 10 2008 030 435.2 filed Jun. 26, 2008, incorporated herein by reference.

The present invention relates to PQQ-dependent glucose dehydrogenases (sPQQGDHs), methods for their production and identification, genes encoding the sPQQGDHs according to the invention, vectors for producing the genes, and also glucose sensors comprising a glucose dehydrogenase according to the invention.

The enzymatic determination of glucose is of great importance in medical diagnostics. Here, the detection of glucose in urine or in blood to diagnose or monitor the progression of metabolic diseases is necessary. In the case of diabetes mellitus, also known as diabetes, it is potentially necessary to determine the blood sugar concentration multiple times each day. This is achieved by the overwhelming number of meters found on the market by an enzymatic method in which glucose is oxidized and the resulting hydrogen ($2H^+$ and $2e^-$) is quantified amperometrically (P. Vadgama, *J. Med. Eng Technol.* 5 [6], 293-298 (1981), K. S. Chua and I. K. Tan, *Clin. Chem.* 24 [1], 150-152 (1978)).

There are a number of different enzymes which are suitable for this purpose, but which work with various cofactors for the primary acceptance of electrons and also have different biochemical properties such as specificity, stability, or conversion rate. The conversion rate of an enzyme is usually reported in activity units (U); in the case of glucose-oxidizing enzymes, the specific activity (U/mg) usually refers to the amount of glucose in micromoles which is oxidized by one milligram of enzyme per minute under defined reaction conditions.

The enzymes often used are glucose dehydrogenases (GDHs). In the case of $NAD(P)^+$-dependent GDH, the cofactor is nicotinamide adenine dinucleotide ($NAD^+$) or nicotinamide adenine dinucleotide phosphate ($NADP^+$) (H. E. Pauly and G. Pfleiderer, Hoppe Seylers. *Z. Physiol Chem.* 356 [10], 1613-1623 (1975)), both fairly unstable compounds which must be added to the reaction, since they are not bound to the enzyme.

A further class of glucose dehydrogenases contains pyrroloquinoline quinone (PQQ) bound to the enzyme as an electron acceptor. Two glucose dehydrogenases of this type which differ structurally from one another have been described: a membrane-anchored form, mPQQGDH (A. M Cleton-Jansen et al., *J. Bacteriol.* 170 [5], 2121-2125 (1988)), and a smaller, soluble form, sPQQGDH (A. M. Cleton-Jansen et al., *Mol. Gen. Genet.* 217 [2-3], 430-436 (1989)). The latter is, owing to its high specific activity, its insensitivity to oxygen, and the tightly bound, stable cofactor, an enzyme which is especially suitable for producing test systems for glucose determination. In a number of commercial blood glucose meters, this enzyme is therefore used, despite a lower substrate specificity which this enzyme exhibits in comparison with the other enzymes mentioned. Owing to the last mentioned limitation, it would of course be desirable to have variants of this enzyme which have a higher substrate specificity.

Apart from the substrate glucose, sPQQGDH also converts other sugars to the corresponding lactone, preferably disaccharides in which the reducing sugar is glucose, but also other reducing sugars. Since such sugars do not normally occur in human blood, an enzyme test based on sPQQGDH generally delivers a result which corresponds to the glucose concentration. However, certain medical therapies involve administration of substances of which one of the breakdown products is maltose, which is oxidized by sPQQGDH and thus contributes undesirably to the measured result (T. G. Schleis, *Pharmacotherapy* 27 [9], 1313-1321 (2007)). In the administration of xylose and galactose in diagnostic methods or as an adjuvant to medicaments, these sugars are themselves measured. It therefore makes sense to suitably suppress the subsidiary activities of sPQQGDH.

In the literature and also in patent specifications, a number of attempts to improve the substrate specificity of sPQQGDH by introducing mutations are described (S. Igarashi et al., *Biomol. Eng* 21 [2], 81-89 (2004)). To this end, single amino acids in the region of the catalytic site (EP1666586A1) but also at other sites in the enzyme (U.S. Pat. No. 7,132,270B2) were substituted by other amino acids by site-directed mutagenesis, or single amino acids were added by insertion (EP1367120A2). Furthermore, combinations of various mutations are described (EP1666586A1, U.S. Pat. No. 7,132, 270B2). In addition, variants have been described in which two amino acids were added at one site in sPQQGDH. However, no significant improvements in substrate specificity could be achieved as a result (WO2006085509).

Despite these results, there is still a need for variants of sPQQGDH, since no variants have yet been described so far which allow sufficient discrimination between glucose and other sugars at a sufficiently high reactivity with glucose. Of importance here is, more particularly, the ability of the enzyme, even in the presence of a mixture of glucose and other sugars, to make the glucose concentration reliably determinable. None of the variants described sufficiently exhibit this property.

In view of the prior art, an object of the invention is thus to provide glucose dehydrogenases which make reliable glucose determination possible, even in the presence of a mixture of glucose and other sugars. More particularly, an object of the invention is to provide glucose dehydrogenases with which glucose can be reliably determined in the presence of maltose. Furthermore, an object of the invention is to provide a method for producing and identifying such glucose dehydrogenases which are especially suitable for glucose determination in the presence of other sugars, more particularly in the presence of maltose.

It has now been found that, surprisingly, sPQQ glucose dehydrogenases in which three to five amino acids are inserted in the region of the substrate-binding region exhibit an improved glucose specificity over the original form of the enzyme.

The present invention accordingly provides sPQQ glucose dehydrogenases having an improved glucose specificity over the original form of the enzyme, characterized in that three to five amino acids are inserted in the region of the substrate-binding region.

The sPQQGDHs according to the invention can be encoded by genes which are obtained by mutagenesis from described wild-type strains occurring in nature, such as *Acinetobacter calcoaceticus* LMD 79.41 (K. Kojima K. et al., *Biotechnology Letters* 22, 1343-1347 (2000)) and also further strains of the genus *Acinetobacter* (P. J. Bouvet P. J. and O. M. Bouvet, *Res. Microbiol.* 140 [8], 531-540 (1989)), more particularly those which have increased thermal stability, such as the *Acinetobacter* sp. strains described in EP1623025A1. Preferred strains are the *Acinetobacter* sp. strains PT16, KOZ62, KOZ65, PTN69, KG106, PTN26, PT15, KGN80, KG140, KGN34, KGN25, and KGN100 described in EP1623025A1; more preferred is the strain KOZ65.

In order to be able to obtain the sPQQGDHs according to the invention, codons must be inserted at the position corresponding to the substrate-binding site in a sPQQGDH gene suitable in such a way. The spatial structure of a number of sPQQGDHs is known and deposited in public databases (A. Oubrie et al., *J. Mol. Biol.* 289 [2], 319-333 (1999); A. Oubrie et al., *EMBO J.* 18 [19], 5187-5194 (1999)). Thus, the distance of individual amino acid positions to the bound substrate can be estimated. Such estimations are, for example, possible with visualization programs for proteins, such as the software program Cn3D, which is available on the Internet (http://www.ncbi.nlm.nih.gov/Structure/CN3D/cn3d.shtml). The sequence of the published X-ray structure is based on the sPQQGDH from *Acinetobacter* calcoaceticus, which is 455 amino acids long. The original form of the more preferred sPQQGDH from the strain KOZ65 has 456 amino acids, just like the enzyme from *Acinetobacter baumannii*. Responsible for this is, in both cases, an additional glutamine residue after position 289. Below, details about the position of individual amino acids relate, nonetheless, to the shorter sequence of sPQQGDH, used in the X-ray structure, from the strain *Acinetobacter* calcoaceticus LMD 79.41. The amino acid located there is reported in the one-letter code for amino acids in front of the position.

Amino acid regions whose distances to the substrate are not greater than 5 angstroms, such as, for example, positions Q76, D143, Q168, Y343 and the respective neighboring amino acid residues, are preferred for mutagenesis. Thus, an insertion of three or more amino acids can be made, for example, before or after one of the positions specified in order to alter the spatial constitution of the substrate-binding site. More preferred is an insertion of additional amino acids between positions Q168 and L169. Variants of KOZ65 having insertions at this site largely showed, surprisingly, distinctly reduced activity on maltose in comparison with glucose. More preferred are sPQQGDHs having the insertion sequences between positions Q168 and L169 listed in table 1. As a comparison, the wild type is shown in the first row. The sPQQGDHs according to the invention have, as outlined in table 1, an increased substrate specificity (lower maltose/glucose ratio and lower value of the interference of glucose in a glucose/maltose mixture).

TABLE 1

| Clone | Sequence of insertion | SEQ ID | Specific activity on glucose [U/mg] | Ratio of activities on maltose/ glucose at 30 mM | Interference (5 mM glucose/ 5 mM maltose) |
|---|---|---|---|---|---|
| Reference: | | | | | |
| wt-GDH KOZ65 | — | | 3000 | 90.0 | 63 |
| 5145-17-E10 | AYQ | 1 | 240 | 7.4 | -5.8 |
| 5145-20-E7 | AWL | 2 | 131 | 10.5 | -4 |
| 5146-08-E9 | AFV | 3 | 236 | 6.5 | -4.7 |
| 5146-10-E4 | GYI | 4 | 351 | 5.9 | -9.9 |
| 5181-09-G12 | AYV | 5 | 738 | 5.4 | -10.8 |
| 5181-13-A12 | AFQ | 6 | 188 | 13.7 | -15.7 |
| 5138-11-A2 | AGRM | 7 | 101 | 9.5 | 15.5 |
| 5152-21-E1 | GLAV | 8 | 166 | 11.7 | -20.7 |
| 5152-20-A7 | MGRFL | 9 | 530 | 7.95 | 5.6 |
| 5381-05-C4 | VSTFF | 10 | 264 | 9.5 | 1.2 |
| 5381-06-C12 | VSKNH | 11 | 229 | 10 | 3.8 |
| 5381-07-F10 | SSRNH | 12 | 203 | 9.5 | 4.2 |
| 5381-09-A11 | SGRIL | 13 | 411 | 6.6 | 5.3 |
| 5386-08-D10 | VGRLT | 14 | 272 | 6.4 | 5.7 |
| 5386-13-F10 | AERNY | 15 | 110 | 7.6 | 0.2 |
| 5386-19-B9 | MESHN | 16 | 111 | 8.2 | 7.8 |
| 5388-15-G8 | VGHVT | 17 | 296 | 6.2 | 3.8 |
| 5388-19-F3 | VGRYQ | 18 | 188 | 7.3 | 4.8 |

The present invention further provides a method for producing and identifying sPQQGDHs which show increased substrate specificity over the wild type. The method according to the invention allows, by means of localized random mutagenesis, the generation of a multiplicity of variants having three, four, five, or more inserted amino acids at a desired site of the sPQQGDH sequence. The enzymes generated are screening for substrate specificity, and the best variants are selected.

The method according to the invention is characterized in that a vector in which a suitable sequence region before and after the desired insertion site has been deleted and replaced by a restriction site unique for this vector is produced in a first step. Into vector DNA which is opened with this restriction enzyme, are inserted in a second step double-stranded oligonucleotide sequences produced by means of PCR amplification and containing the desired insertion in addition to the sequence deleted in the vector, resulting in a gene product which contains, with regard to its amino acid sequence, no further alterations other than the insertion of three or more amino acids at the desired site. The double-stranded fragment PCR produced from synthetic oligonucleotides which is to be inserted contains the three or more additional randomized codons for altering substrate specificity, but also the codons which were deleted in the vector. The codons selected to this end are particularly well expressible E. coli. Besides the insertion region, the nucleotide sequence therefore differs from that of the sPQQGDH gene from KOZ65, but not the amino acid sequence.

With the insertion of three additional amino acids, 8000 enzyme variants are conceivable; with four additional amino acids, the number is 160,000; and with five additional amino acids, there are 3.2 million variants. The synthesis of mutagenic oligonucleotides can therefore make use of, in addition to completely randomized sequences, such sequences as contain, at some or all positions, degenerate codons for each of the amino acids to be inserted. This can be used in order to reduce the number of possibilities overall, to avoid stop codons, or to favor individual amino acids at particular positions.

In a third step of the method according to the invention, recombinant vectors which have been produced as described above are transformed into suitable host bacteria, and the host bacteria are propagated in a suitable growth medium. The procedures for cloning genes from microorganisms and their expression in another host and also the techniques for isolating and altering nucleic acids are known to a person skilled in the art (see, for example, *Molecular Cloning—A Laboratory Manual; Vol.* 1; Sambrook, J. and Russel, D. W.; 3rd edition, CSHL Press 2001). Growing microorganisms and purifying recombinant enzymes therefrom are also known in the prior art (see ibid.; Vol. 3).

In a fourth step of the method according to the invention, the bacterial colonies are tested with regard to their activity toward various sugars and the best are identified. According to the invention, not only is a test done here with regard to the activity toward the individual sugars, but also with regard to the interference of various sugars.

The activities can be determined as specific activities, i.e., conversion rates which are turned by a defined amount of enzyme per unit time. In the case of glucose-oxidizing enzymes, the specific activity (U/mg) usually refers to the amount of glucose in micromoles which is oxidized by one milligram of enzyme per minute under defined reaction conditions. Glucose is generally present in an excess over the enzyme in order to eliminate the influence of glucose concentration on the reaction rate. The conversion rate is ascertained by tracking the breakdown of a reagent or the formation of a product over time. Tracking over time can be done photometrically for example. To ascertain reaction rates and conversion rates, reference may be made to textbooks of physical chemistry (e.g., Peter Atkins, *Physical Chemistry*, W.H. Freeman & Co; 7th edition, 2002).

Initially, the individual colonies are divided, and an enzyme test (ascertaining specific activity) with glucose as a substrate and a second enzyme test with a second sugar, maltose for example, as a substrate are carried out. In the case of colonies having the highest activities toward glucose while having at the same time the lowest activities toward the second sugar (e.g., maltose), the activity toward a mixture of glucose and the second sugar (e.g., maltose) is also determined. This is because it emerged in particular in the investigation of some variants having very low relative reactivity on maltose as the only substrate that, surprisingly, this property of a variant is not always accompanied by an independent property, namely the reliable discrimination of glucose and maltose when both sugars are present as a mixture. This can lead to both overestimation and underestimation of the glucose concentration present in this mixture. In the search for enzymes which are to be used to determine glucose concentrations in samples, a high glucose specificity on mixtures of glucose and other sugars is therefore of decisive importance, or put another way, a very low interference of the sugar in question. The interference of a sugar is calculated from the enzyme activity which is measured on a mixture of glucose and interfering sugar minus the activity which is measured on the same concentration of glucose alone, normalized to this glucose activity (see equation 1).

$$I = \frac{V_{Mixture} - V_{Reference}}{V_{Reference}} \quad \text{(equation 1)}$$

In equation 1, I is the interference of glucose with another sugar, $V_{Reference}$ is the rate at which glucose is broken down by the enzyme observed, and $V_{Mixture}$ is the rate at which glucose is broken down in a mixture with the other sugar. The rates can be, for example, determined photometrically (see, for this purpose, examples 3, 4, 7, and 9).

Positive values in this context mean that the enzyme activity on a mixture is higher than on glucose alone i.e., both sugars are evidently oxidized. Negative values can be interpreted to the effect that the interfering sugar is also oxidized, but that the activity of the enzyme for glucose is reduced as a result. Both effects are undesirable for an enzyme which is to be used to specifically quantify glucose.

The method according to the invention allows production and identification of variants of sPQQGDH in which substrate specificity is altered compared with the original form of the enzyme. The method according to the invention can also be modified and/or expanded to the effect that, instead of substrate specificity or in addition to it, other biochemical properties, such as, for example, thermal stability, are tested and, thus, improved variants compared with the original form and with regard to the other biochemical properties are identified. The method according to the invention thereby makes it possible to select variants of sPQQGDH having especially advantageous properties.

The present invention also provides genes which encode the sPQQGDHs according to the invention and vectors for generating the genes.

The present invention further provides a glucose sensor comprising an sPQQGDH according to the invention for determining glucose. The design and the mode of operation of glucose sensors based on glucose dehydrogenases are known to a person skilled in the art from the prior art (see, for example, EP1146332 A1). According to that, such a glucose sensor comprises an electrode system consisting of a working electrode, a counter electrode, and a reference electrode on an isolating plate, and supporting an enzymatic reaction layer which contains a glucose dehydrogenase and an electron acceptor in contact with the electrode system.

Suitable working electrodes include carbon, gold, platinum, and similar electrodes on which an enzyme according to the invention is immobilized by means of a crosslinking agent: embedding in a polymer matrix, encasing with a dialysis membrane, using a photocrosslinkable polymer, an electrically conductive polymer, or a redox polymer, fixing the enzyme in a polymer or adsorbing on the electrode with an electron mediator including ferrocene or derivatives thereof or any combination thereof. sPQQGDHs according to the invention are preferably immobilized on the electrode in the form of a holoenzyme, although they can also be immobilized as an apoenzyme and PQQ is provided as a separate layer or in a solution. sPQQGDHs according to the invention are usually immobilized on a carbon electrode with glutaraldehyde and then treated with an amine-containing reagent in order to block the glutaraldehyde. A platinum electrode, for example, can be used as a counter electrode, and a Ag/AgCl electrode, for example, can be used as a reference electrode.

The glucose amount can be measured as follows: PQQ, $CaCl_2$, and a mediator are added to a thermostat cell which contains a buffer and left at a constant temperature. Suitable mediators include, for example, potassium ferricyanide and phenazine methasulfate. An electrode on which an sPQQGDH according to the invention has been immobilized is used as a working electrode in combination with a counter electrode (e.g., a platinum electrode) and a reference electrode (e.g., Ag/AgCl electrode). After a constant voltage has been applied to build up a steady current at the working electrode, a glucose-containing sample is added in order to measure the rise in current strength. The glucose amount of the sample can be read off from a calibration curve established with glucose solutions in standard concentrations.

The invention is explained below in more detail with the aid of examples, but without restricting it to the examples.

EXAMPLES

The chemicals cited in the following examples are commercially available, from Sigma-Aldrich for example and from the companies specified in each case.

Example 1

Producing a Vector for Inserting Additional Amino Acids Between Q168 and L169

To produce variants according to the invention, a gene for an sPQQGDH must be available in an expression plasmid which can be propagated in microorganisms allowing the induced expression of the sPQQGDH and which can be used to carry out the desired mutations. A multiplicity of plasmids and microorganisms which can be used for this purpose are known to a person skilled in the art. In this and all further examples, a construct based on the commercially available vector pASK-IBA3 (IBA GmbH, Gottingen) was used. The sPQQGDH gene from the strain *Acinetobacter* sp. KOZ65 was cloned into pASK-IBA3 as follows. A 1.46 kb long DNA fragment was generated from genomic DNA of *Acinetobacter* sp. KOZ65 with the two oligonucleotides GDH-U3 (5'-TGGTAGGTCTCAAATGAATAAACATTTATTGGC TAAAATTAC-3; SEQ ID 19) and GDH-L5 (5'-TTCAGCTCTGAGCTTTATATGTAAATCTAATC-3'; SEQ ID 20) with the help of a PCR reaction (Phusion DNA Polymerase, Finnzymes Oy) according to the specifications of the manufacturer. The fragment was cleaned up and subsequently incubated with the restriction enzyme BsaI. The vector pASK-IBA3 was opened with the restriction enzyme HindIII. The restriction enzyme was denatured by heat treatment and the resulting DNA overhangs were filled with T4 DNA polymerase in the presence of dATP, dCTP, dGTP, and dTTP. The DNA was subsequently cleaned up and incubated with the restriction enzyme BsaI. The 114 bp long fragment thus released was discarded; the PCR amplicon with the sPQQGDH gene from KOZ65 was ligated into the 3.1 kb long vector fragment. The ligation product was transformed into competent cells of the *E. coli* strain DH5α. The vector pAI3B-KOZ65 produced this way is suitable for inducible expression of sPQQGDH of the type KOZ65. The nucleotide sequence of the vector pAI3B-KOZ65 is reported under SEQ ID 21; the amino acid sequence of the sPQQGDH encoded by it is reported under SEQ ID 22.

In order to be able to insert three or more amino acids between Q168 and L169, the vector pAI3B-KOZ65-U was initially produced. To this end, plasmid DNA of the vector pAI3B-KOZ65 was used as a template for a PCR amplification A with the primers IBA-For (5'-TAGAGTTATTTTAC-CACTCCCT-3'; SEQ ID 23) and Eco109-Up (5'-GGTTAG-GTCCCTGATCACCAATCG-3'; SEQ ID 24) and also a PCR amplification B with the primers BfuA-US1 (5'-CACAGG-TACACCTGCCGCCACT-3'; SEQ ID 25) and Eco109-Down (5'-TACGAGGACCCAACAGGAACTGAGC-3'; SEQ ID 26). The amplicon resulting from A was cleaned up and cut with the restriction enzymes XbaI and EcoO109I. The resulting 588 base pairs (bp) long fragment was isolated. The amplicon resulting from B was cleaned up and cut with the restriction enzymes BfuAI and EcoO109I. The resulting 353 bp long fragment was also isolated. The vector pAI3B-KOZ65 was cut with the restriction enzymes BfuAI and XbaI. The resulting 3567 bp long fragment was isolated on an agarose gel. Kits and reagents from New England Biolabs GmbH (Frankfurt), Invitrogen (Karlsruhe), Qiagen (Hilden), and Roche Diagnostics (Mannheim) were used according to the specifications of the manufacturers for the steps outlined. Additional procedures were obtained from the collection of procedures by Sambrook and Russell (*Molecular Cloning—A Laboratory Manual*; Sambrook, J. and Russel, D. W.; 3rd edition, CSHL Press 2001).

The three fragments were subsequently ligated and transferred into *E. coli*-DH5α by chemical transformation. Plasmid DNA was prepared from 12 colonies and subsequently checked by appropriate restriction digests to determine whether the desired plasmid had resulted, as was the case in 9 isolates. By sequencing four of these clones, it was confirmed that, in all cases, no further alterations other than those outlined in FIG. 1e had taken place.

The vector pAI3B-KOZ65-U (SEQ ID 27) contains only one unique EcoO109I restriction site (RG'GNCCY). EcoO109I generates 3 bp long 5' overhangs in which the middle nucleotide is any nucleotide; in the case of pAI3B-KOZ65-U, it is an A on the coding strand. The DNA encoding amino acids R166 to P182 and also a further nucleotide are deleted in pAI3B-KOZ65-U, leading to a shift in reading frame. An attempt to express this gene therefore leads to a shortened polypeptide having no function (SEQ ID 28). The vector is suitable for the incorporation of synthetic, double-stranded DNA fragments which lead to restoration of a functioning sPQQGDH gene having insertions between positions Q168 and L169, as described in more detail in example 2.

Example 2

Producing sPQQGDH Insertion Mutants

Figure 2:
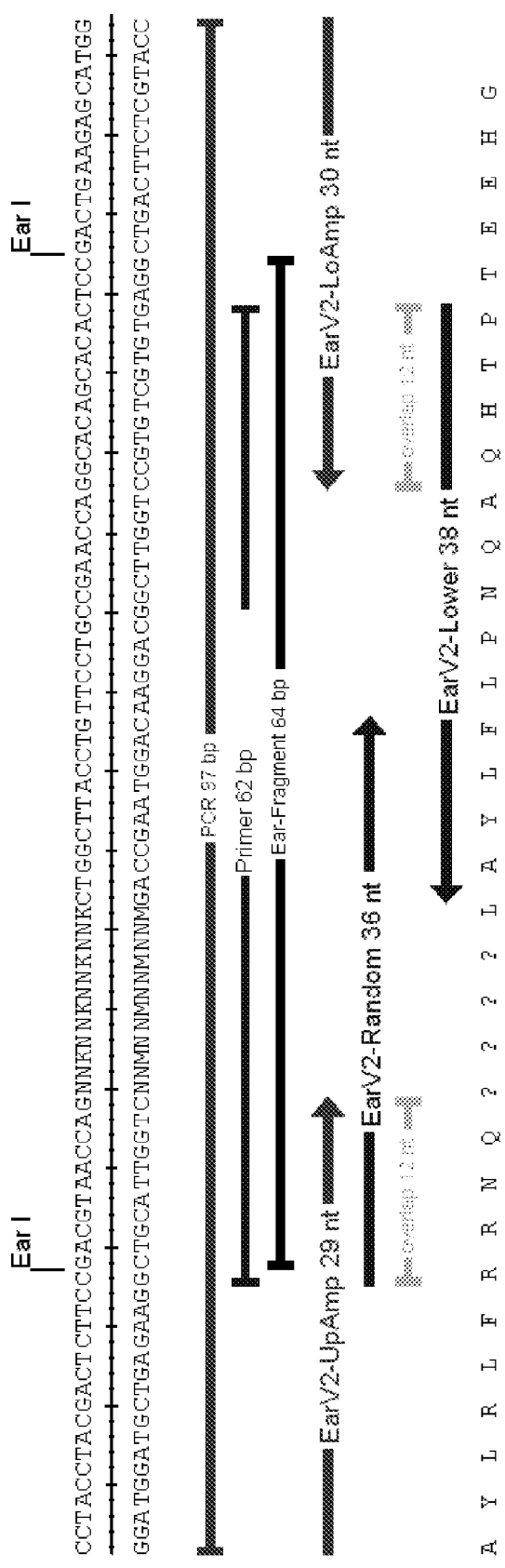

To produce insertion mutants having four additional amino acids between positions Q168 and L169, four synthetic oligonucleotides were used: EarV2-Random (5'-CGACG- TAAC-CAGNNKNNKNNKNNKCTGGCTTACCTG-3'; SEQ ID NO: 29), EarV2-Lower (5'-GTGTGCTGTGCCTGGT-TCGGCAGGAACAGGTAAGCCAG-3'; SEQ ID NO: 30), EarV2-UpAmp (5'-CCTACCTACGACTCTTCCGACG-TAACCAG-3'; SEQ ID NO: 31), and EarV2-LoAmp (5'-CCAT-GCTCTTCAGTCGGAGTGTGCTGTGCC-3'; SEQ ID NO: 32). In FIG. 2, the strategy for producing a double-stranded insertion fragment from these oligonucleotides is schematically illustrated. The sequence of the four amino acids to be inserted is, in this case, randomized: NNK NNK NNK NNK. N is a mixture of all four nucleotides (dATP (A), dCTP (C), dGTP (G), dTTP (T)) in the synthesis of the oligonucleotide at the respective position, while K is G or T. The sequence NNK makes it possible to have codons for all 20 amino acids, but for only one of the three stop codons, lowering the likelihood of incomplete gene products. Other combinations of nucleotides at the individual positions are freely selectable in order, for example, to limit the possible amino acids at a codon position. Oligonucleotide EarV2-Random contains the sequence encoding R166 to L172; the oligonucleotide EarV2-Lower representing the complementary strand overlaps in the region of L169 to L172 and reaches as far as T181. Oligonucleotide EarV2-UpAmp overlaps for 12 bp at the 3' end with the 5' end of oligonucleotide EarV2-Random, while oligonucleotide EarV2-LoAmp likewise overlaps for 12 bp at the 3' end with the 5' end of oligonucleotide EarV2-Lower. The last two oligonucleotides mentioned each contain an EarI restriction site (CTCTTCN'NNN).

First, the oligonucleotides EarV2-Random and EarV2-Lower were heated up to 90° C. and cooled down over 5 minutes to 10° C. in the presence of 10 mM Tris.HCl, pH 7.9 at 25° C., 10 mM $MgCl_2$, 50 mM NaCl, 1 mM dithiothreitol (buffer NEB2) in a PCR machine (GeneAmp 9600, Perkin-Elmer). The partially double-stranded pieces of DNA formed as a result were, after addition of all four DNA nucleotides and the Klenow fragment of the DNA polymerase from E. coli, synthesized to complete double strands by incubation for 15 minutes at room temperature. Afterwards, the reaction mixture was introduced into a PCR reaction with the oligonucleotides EarV2-UpAmp and EarV2-LoAmp in order to amplify the double strand obtained. Since the overlapping of the amplifying oligonucleotides EarV2-UpAmp and EarV2-LoAmp with the newly formed double strand is only 12 bp in each case, the first two amplification cycles were not carried out with the thermostable polymerase of the PCR kit but with the Klenow fragment of the DNA polymerase from E. coli in order to achieve the binding of the oligonucleotides EarV2-UpAmp and EarV2-LoAmp used as primers. To this end, the starting reaction was brought to 94° C. for 1 minute and subsequently placed on ice. Then, 1 μL of DNA polymerase (Klenow fragment) was added and incubated for 3 minutes at 18° C. and for 1 minute at 25° C. Afterwards, the starting reaction was again brought to 94° C. for 1 minute and subsequently placed on ice; 1 μL of DNA polymerase (Klenow fragment) was added and incubated for 3 minutes at 18° C. and for 1 minute at 25° C. Only then was the following amplification program carried out (20 cycles) in the PCR machine: 1 minute at 94° C., 1 minute at 52° C., 1 minute at 72° C.

After PCR amplification, the reaction was cleaned up by column chromatography (PCR Purification Kit, Qiagen) and cut with EarI. The reaction mix was subsequently separated on an agarose gel (4% agarose), and the desired 64 bp fragment (SEQ ID NO: 33) was isolated from the gel and cleaned up.

The vector pAI3B-KOZ65-U described in example 1 was cut with EcoO109I and subsequently dephosphorylated with alkaline phosphatase according to manufacturer specifications (New England Biolabs) in order to prevent recirculization of the vector. The 64 bp fragment and the dephosphorylated vector linearized with EcoO109I were subsequently ligated in a ratio of 5 to 1 overnight at 16° C. The 5' overhangs formed by EcoO109I and EarI are compatible in the sense that the 64 bp fragment can be ligated into the vector in the desired orientation relative to the vector, but not in the other orientation. Ligation products having incorrectly orientated insertions are thus excluded, but not the formation of multimers having the correct orientation in each case. Such genes, however, do not lead to expression of functional sPQQGDH proteins since a shift in reading frame occurs. The resulting ligation product was transformed into E. coli-DH5α. From the initial transformation mix, $\frac{1}{25}$, $\frac{4}{25}$, and $\frac{20}{25}$ were each plated on a 20 cm×20 cm agar plate in order to achieve, with at least one dilution, a colony density of about 1000-5000 colonies per plate.

This example outlines the production of a library whose clones express sPQQGDH variants having, in each case, four additional amino acids. The production of libraries having other lengths of the insertion was carried out in the same way.

Example 3

Screening a Variant Library

To select suitable variants from a library produced according to the method described in example 2, 2200 colonies were picked from two agar plates having a total of about 4000 colonies with the help of the automated colony picker QPix (Genetix) and transferred into microtiter plates (MTPs) having, in each case, 200 μL of LB medium with ampicillin at 100 μg/mL per well. A total of eight wells on 4 MTPs were additionally inoculated with cultures of the original strain E. coli-DH5α::pAI3B-KOZ65. The MTPs were sealed with a gas-permeable film (Airpore Sheets, Qiagen) and shaken for 5 hours at 37° C. Subsequently, 50 pt of each individual culture were transferred into a new well, also in a MTP, in which 150 pt of LB medium with ampicillin were present. To this end, use was made of a pipetting robot which performs 96 pipetting operations in parallel. This medium received additionally 200 ng/mL of anhydrotetracycline in order to induce the expression of the sPQQGDH gene. These MTPs were shaken overnight at 28° C.

In order to be able to assess the enzyme activity of a large number of colonies, use was made of a test in which disruption of the cells is not necessary: after activation of the enzyme by addition of PQQ, the oxidation of the sugar can be directly tracked owing to the decolorization of dichlorophenolindophenol (DCPIP) upon its reduction. For screening, 40 μL of the induced culture from each well were mixed with 60 μL of glucose test solution and a further 40 μL were mixed with 60 μL of maltose test solution, any one MTP containing either only glucose test solution or only maltose test solution. The pipetting robot was used for this also. In this way, it was possible to assign to each individual culture a continuously unchanged position on all culture and measurement plates. The glucose test solution contained the following components (in brackets: final concentration in the starting measurement solution): 50 mM glucose (30 mM), 750 μM DCPIP (450 μM), 1.5 μM PQQ (0.9 μM), 1 mM $CaCl_2$ (0.6 mM), 0.1% $NaN_3$ (0.06%), silicone defoamer (Fluka # 85390) at 62.5 ppm (37.5 ppm), 50 mM tris(hydroxymethyl)aminomethane hydrochloride (Tris.HCl), pH 7.6 (30 mM). In the case of the maltose test solution, no glucose was present, but maltose was present at the same concentration.

Figure 3:
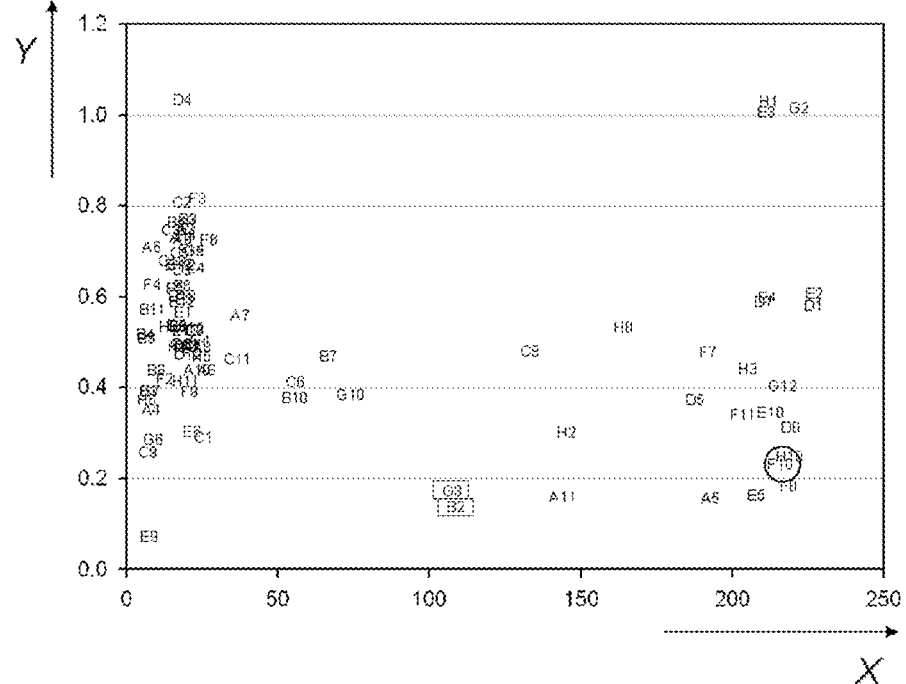
Figure 3:
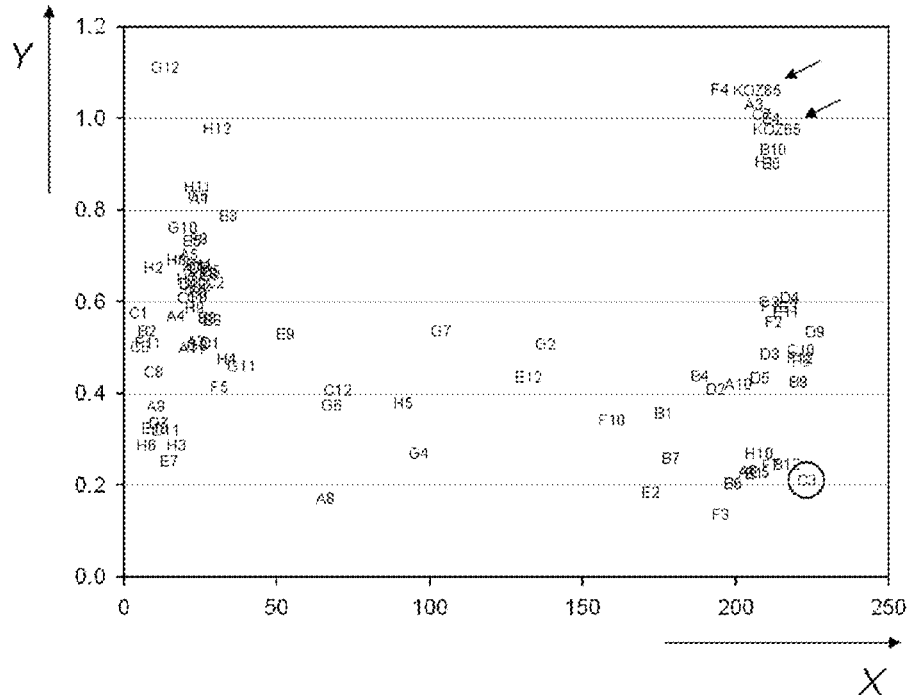

For each MTP having cultures, two measurement plates were generated in this way, one for glucose, the other for maltose. For each measurement plate, the optical density was determined at a wavelength of 605 nm at various time points after the mixing of culture and test solution (Eppendorf-Biophotometer): after 1 minute, after 7 minutes, after 12 minutes, and after 18 minutes. In this way, it was possible to record for each originally isolated colony the enzyme kinetics for glucose as a substrate and the enzyme kinetics for maltose as a substrate. From this, it was possible to ascertain both the relative activity of the clones among one another with glucose as a substrate and the ratio of the activities on glucose and maltose for each individual clone. FIG. 3 shows the result of such a measurement for the MTPs 13 and 22 from the screening of a library having five additional amino acids between positions Q168 and L169. It is apparent that about ⅔ of the tested colonies have a glucose conversion of less than 50 relative units, lying below the readout accuracy of the test. In these colonies, no significant expression of sPQQGDH is detectable, which is attributable to too low a growth of the culture, poor induction of the sPQQGDH gene, unproductive double insertions, or insertion of amino acid combinations which no longer allow enzymatic activity of the protein formed. Of the remaining colonies, the overwhelming proportion exhibit a lower activity on maltose in comparison with glucose. Results from primary screenings as shown in FIG. 3 show a similar high conversion rate of many variants in comparison with the original clone E. coli-DH5α::pAI3B-KOZ65. The relative activity should, however, always be checked since this test, designed for very many individual measurements, cannot differentiate above a certain conversion rate. sPQQGDH from variants generally has a lower conversion rate compared with the sPQQGDH from KOZ65 than would be expected from the screening shown.

Example 4

Refined Screening of Individual Colonies

Figure 4:
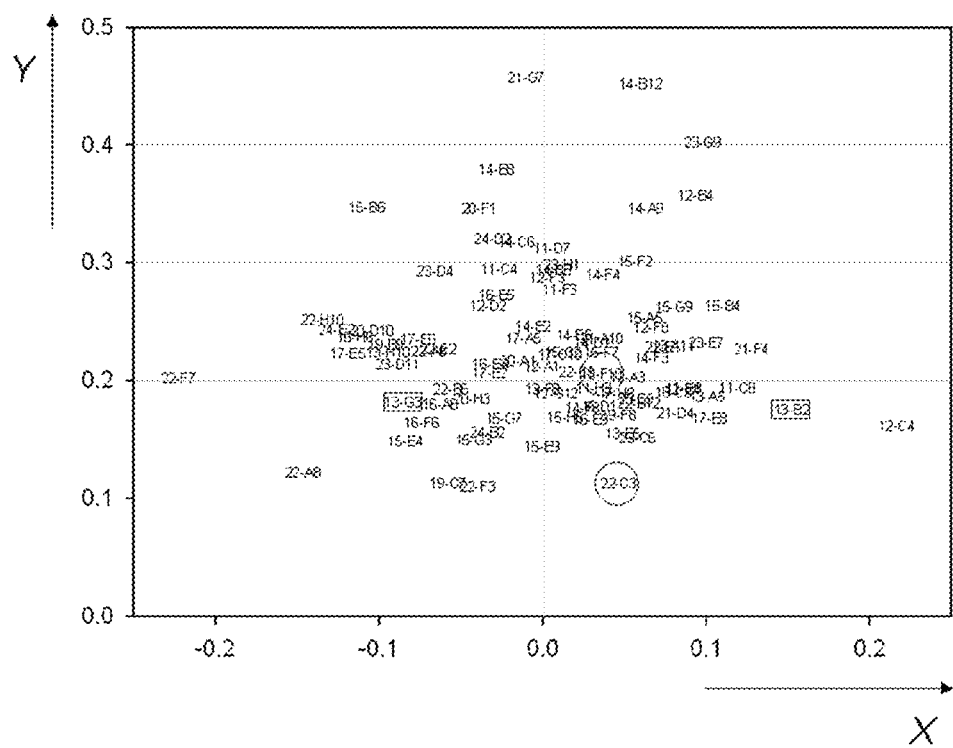

Screening as described in example 3, was used to select 188 colonies in which both the activity on glucose and the ratio of the activities on glucose or maltose appeared particularly promising, and these colonies were arranged on two new MTPs together with cultures of the original strain E. coli-DH5α::pAI3B-KOZ65 and initially grown at 37° C. and then induced overnight at 28° C. as described in example 3. For induction, two plates were set up from each MTP in order to obtain sufficient culture volume for the screening experiment. After induction, the cultures grown in parallel, each of about 200 μL, were combined and mixed. From each of these induced cultures, 40 μL were transferred in each case to measurement plates in which 60 μL of the test solution described in example 3 were present in each case, but with the following sugars: G—50 mM glucose, M—50 mM maltose, GM—50 mM glucose and 50 mM maltose, GGal—50 mM glucose and 50 mM galactose, or GXyl—50 mM glucose and 50 mM xylose. These plates were immediately measured after the mixing of culture and measurement solution over 30 minutes in intervals of 30 seconds in order to obtain the kinetics of each individual culture. From the data thus obtained, the rate of conversion on glucose and maltose alone, the ratio of the activities on glucose and maltose, and, in particular, the influence of maltose, galactose, and xylose on the conversion of glucose (interference) can be estimated for each culture. In FIG. 4, the result of this follow-up investigation of selected colonies (2nd screening) for the screening depicted in example 3 is displayed.

Two colonies of MTP 13 of the first screening (13-G3 and 13-B2; each marked with a rectangle in FIGS. 3 and 4) show by way of example that colonies having a promising ratio of maltose activity to glucose activity (FIG. 3) can exhibit strongly deviating interference behavior: 13-G3 experiences negative interference by maltose; 13-B2 experiences positive interference. In total, 28 colonies were selected for further investigation on the basis of both screenings depicted.

Example 5

Growing Strains which Express Variant Forms of sPQQGDH

First, a preculture was produced as follows from each of four selected colonies of a library having in each case three additional amino acids between positions Q168 and L169: 2 mL of TB medium (with 100 μg/mL ampicillin) were inoculated with the colony to be checked and shaken overnight at 37° C. and 225 rpm. For the main culture, 50 mL of TB medium (100 μg/mL ampicillin) were inoculated with the fully grown preculture. The culture was shaken at 37° C. and 225 rpm until an optical density of about 1 at 605 nm ($OD_{605}$) was achieved. Then, the expression of the enzyme was induced by addition of an anhydrotetracycline (AHT) stock solution. To this end, the inducer was dissolved in DMF. The final concentration of AHT in the culture was 0.2 μg/mL; the induction took place over 24 hours at 27° C. and 225 rpm. The cells were harvested by centrifugation of the main culture at 3220×g for 15 minutes at 4° C.

The pelleted cells were, depending on amount, resuspended in 10-20 mL of 50 mM 3-morpholinopropane-1-sulfonic acid buffer (MOPS), pH 7.6, and 2.5 mM $CaCl_2$ and solubilized by ultrasonication until a distinct clarification of the cell suspension was observable. Cell debris and any inclusion bodies present were centrifuged down at 48,745×g for 10 minutes at 4° C.

Example 6

Cleanup of the sPQQGDH Variants

The supernatants from example 5 were diluted with column buffer (10 mM MOPS, pH 7.6+2.5 mM $CaCl_2$) 1:5 to 10 or 50 mL and resolved chromatographically over a cation exchanger (Toyopearl CM-650M, TOSOH BIOSEP GmbH). For this purpose, a 10×1.42 cm column having about 16 mL of column bed is used; the flow rate was 4 mL/minute. The column was equilibrated with 10 column volumes of buffer; afterwards, the sample was applied. The column was washed with 4 column volumes of buffer; subsequently, the sPQQGDH was eluted by means of a linear salt gradient from 0 to 0.4 M NaCl in column buffer, and the eluate was collected in fractions of 1 or 3 mL. sPQQGDH eluted under these conditions as a virtually homogenous protein, so no further cleanup was necessary. To determine protein, the $OD_{280}$ of the solution was determined With cleaned-up sPQQGDH protein from KOZ65, it had previously been established by gravimetric analysis that the $OD_{280}$ of a 1 mg/mL sPQQGDH solution (PQQ-free apoenzyme) is 1.27.

Example 7

Ascertaining the Enzyme Activity of sPQQGDH Variants

To accurately determine enzymatic activity, the following test was used. Of the enzyme solutions to be investigated, a dilution series in the following buffer was made in each case: 50 mM 1,4-piperazinediethanesulfonic acid (PIPES), pH 6.5, 0.1% Triton X-100, 1 mM CaCl$_2$, 0.1% bovine serum albumin (BSA), and 3 µM PQQ. The sugar serving as a substrate, the electron mediator N-methylphenazonium methasulfate (PMS), and the detection reagent nitro blue tetrazolium chloride (NBT) were prepared separately: 11.7 mL of a solution with 50 mM PIPES, pH 6.5, and 2% Triton X-100 in double-distilled water were mixed with 450 µL of 0.9 M D-glucose, 450 µL of 6 mM PMS, and 450 µL of 6.6 mM NBT (all substances also dissolved in double-distilled water), kept in the dark at 25° C., and used up within an hour. When the enzyme activity on sugars other than glucose is to be measured, these sugars, instead of glucose, are used at a concentration of 0.9 M. The final concentrations of the individual reactants in the measurement solution were: 30 mM sugar substrate, 200 µM PMS, and 220 µM NBT. The prewarmed test solution (725 µL) was mixed with 25 µL of diluted enzyme solution in a cuvette, and the development of formazan was tracked at 570 nm and 25° C. over 3 minutes. The conversion of 1 µmol of glucose results in 0.5 µmol of formazan, of which the molar extinction coefficient is $\epsilon=40,200$ M$^{-1}$cm$^{-1}$. Thus, the enzyme concentration in the sample can be ascertained via the following relation: 1 U/mL sPQQGDH corresponds to a change in the OD$_{570}$ of 1.493 min$^{-1}$. A dilution series of the individual samples is necessary because measurements in which values lower than 0.05 U/mL or greater than 0.7 U/mL are found must be discarded, since sufficient linearity of measurement cannot be ensured outside this range. The concentration of the original sample was then calculated, taking into consideration the dilution levels used. The results are displayed in table 2 below.

TABLE 2

| Clone | Volume [mL] | Enzyme [mg/mL] | Enzyme activity on glucose [U/mL] | Enzyme activity on maltose [U/mL] | Maltose [U/mL]/ glucose [U/mL] | Specific activity [U/mg] |
|---|---|---|---|---|---|---|
| 5146-10-E4 | 6 | 0.124 | 43.6 | 2.6 | 0.059 | 351.6 |
| 5146-08-E9 | 3 | 0.044 | 10.4 | 0.68 | 0.065 | 236.4 |
| 5145-20-E7 | 3 | 0.036 | 4.7 | 0.495 | 0.105 | 130.6 |
| 5145-17-E10 | 5 | 0.053 | 12.7 | 0.935 | 0.074 | 239.6 |

Example 8

Determining the Insertion Sequence

In order to ascertain the actual amino acids inserted between positions Q168 and L169 in a variant of interest, plasmid DNA was prepared from the strain concerned with the help of the QiaPrep Plasmid Isolation Kit (Qiagen, Hilden) according to the specifications of the manufacturer, and the DNA sequence at the insertion site was ascertained from both directions with the oligonucleotides 4472-US1 (5'-CACCGTTAAAGCTTGGATTATC-3'; SEQ ID 34) and 4831-DS1 (5'-CCTTCATCGAAAGACCATCAG-3'; SEQ ID 35) used as primers. The 3' end of the sequence of 4472-US1 is located 58 bp upstream of the insertion site; the 3' end of the sequence of 4831-DS1 is located 82 bp downstream of the insertion site. The results of the sequence analysis are listed in table 3 below.

TABLE 3

| Clone | Nucleotide sequence (-CAG NNK NNK NNK CTG-) | Derived amino acid sequence |
|---|---|---|
| 5146-10-E4 | -CAG GGT TAT ATT CTG- | -Q G Y I L- |
| 5146-08-E9 | -CAG GCT TTT GTT CTG- | -Q A F V L- |
| 5145-20-E7 | -CAG GCT TGG CTG CTG- | -Q A W L L- |
| 5145-17-E10 | -CAG GCT TAT CAG CTG- | -Q A Y Q L- |

For orientation, the flanking amino acids 168Q and 172L (previously 169L) and their codons are also shown.

Example 9

Ascertaining Interference by Sugars Other than Glucose

While a substrate concentration of 30 mM in the starting test solution is usually used in the determination of the specific activity of sPQQGDH, a lower concentration of the sugar in question is sensible for ascertaining interference; around the order of magnitude as occurs in potential subsequent applications. The physiological concentration of glucose in blood is about 100 mg/dL, corresponding to about 5.6 mM. For this reason, the experiments depicted below were carried out with a glucose concentration of 100 mg/dL and 50 to 250 mg/dL of the interfering sugar. In some cases, however, other concentrations and ratios of both sugars to one another were also investigated.

Figure 5:
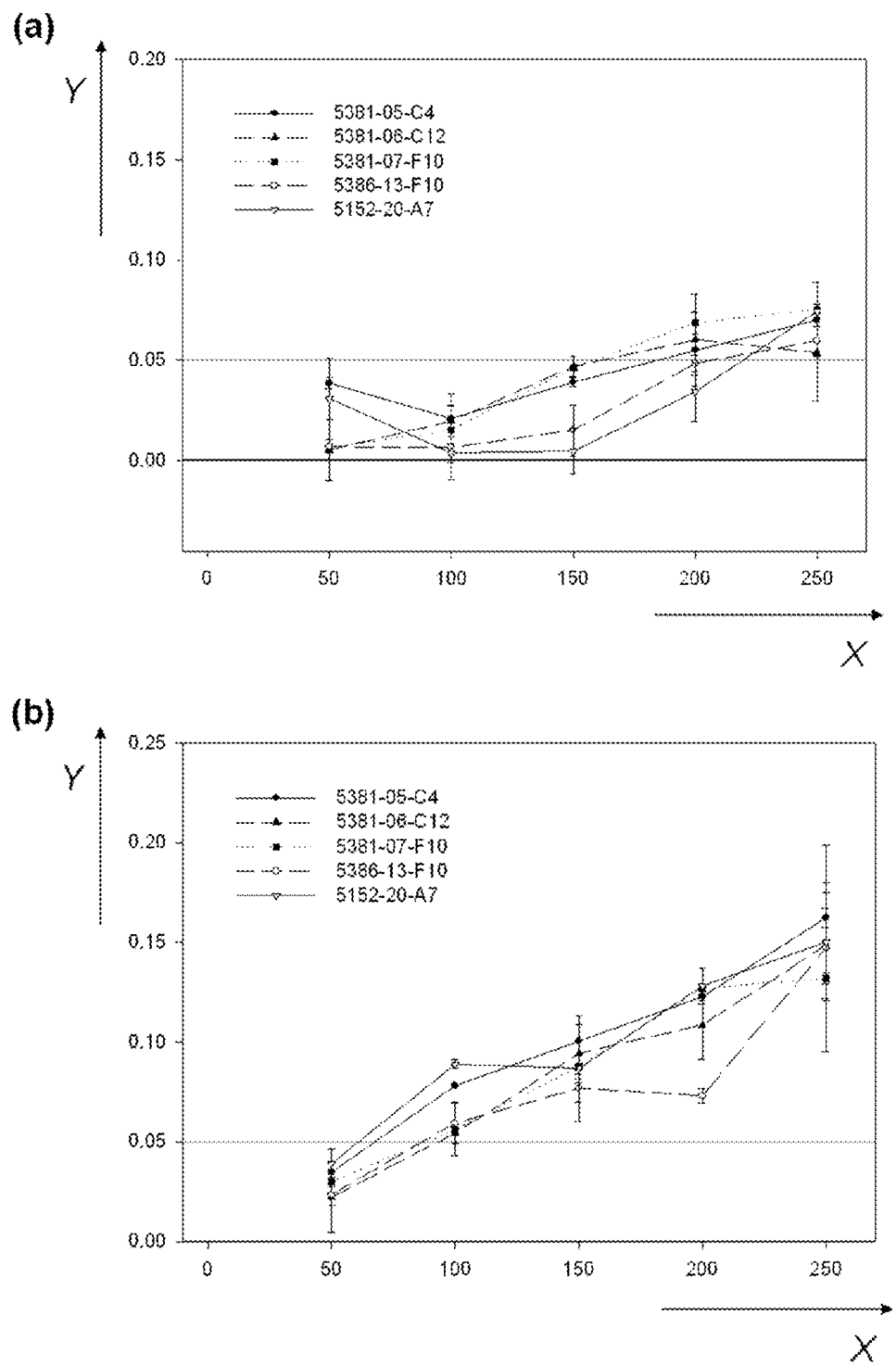
Figure 5:
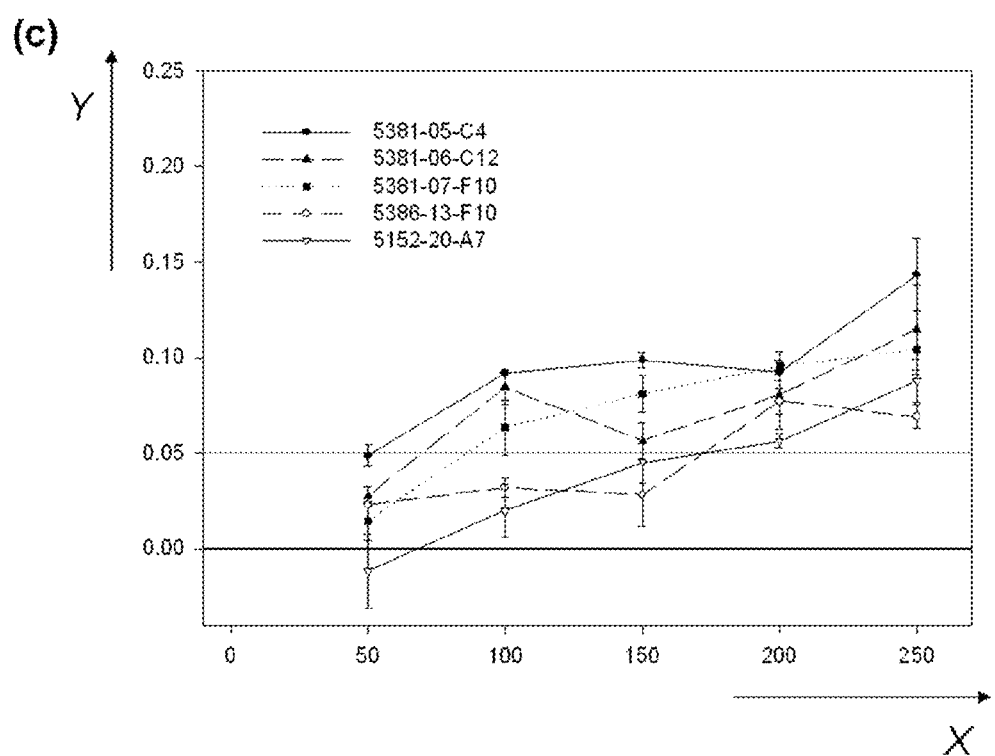

In FIG. 5, the result of an interference measurement of five different variants is displayed. 5381-06-C12, 5381-05-C4, and 5381-07-F10 originate from a library having four additional amino acids between positions Q168 and L169; 5152-20-A7 and 5386-13-F10 originate from a library having five additional amino acids between positions Q168 and L169. In all cases, only a minimal influence of the sugar tested is still detectable: in the case of maltose, measurement with all the clones is not influenced by more than 8%, even at 250 mg/dL maltose (1.3-fold molar amount in comparison with glucose). With galactose, interference is a maximum of 16%, and with xylose, it is a maximum of 14%.

Example 10

Comparison of Interferences of Different Sugars with KOZ65 and Clone 5152-20-A7

Figure 6:
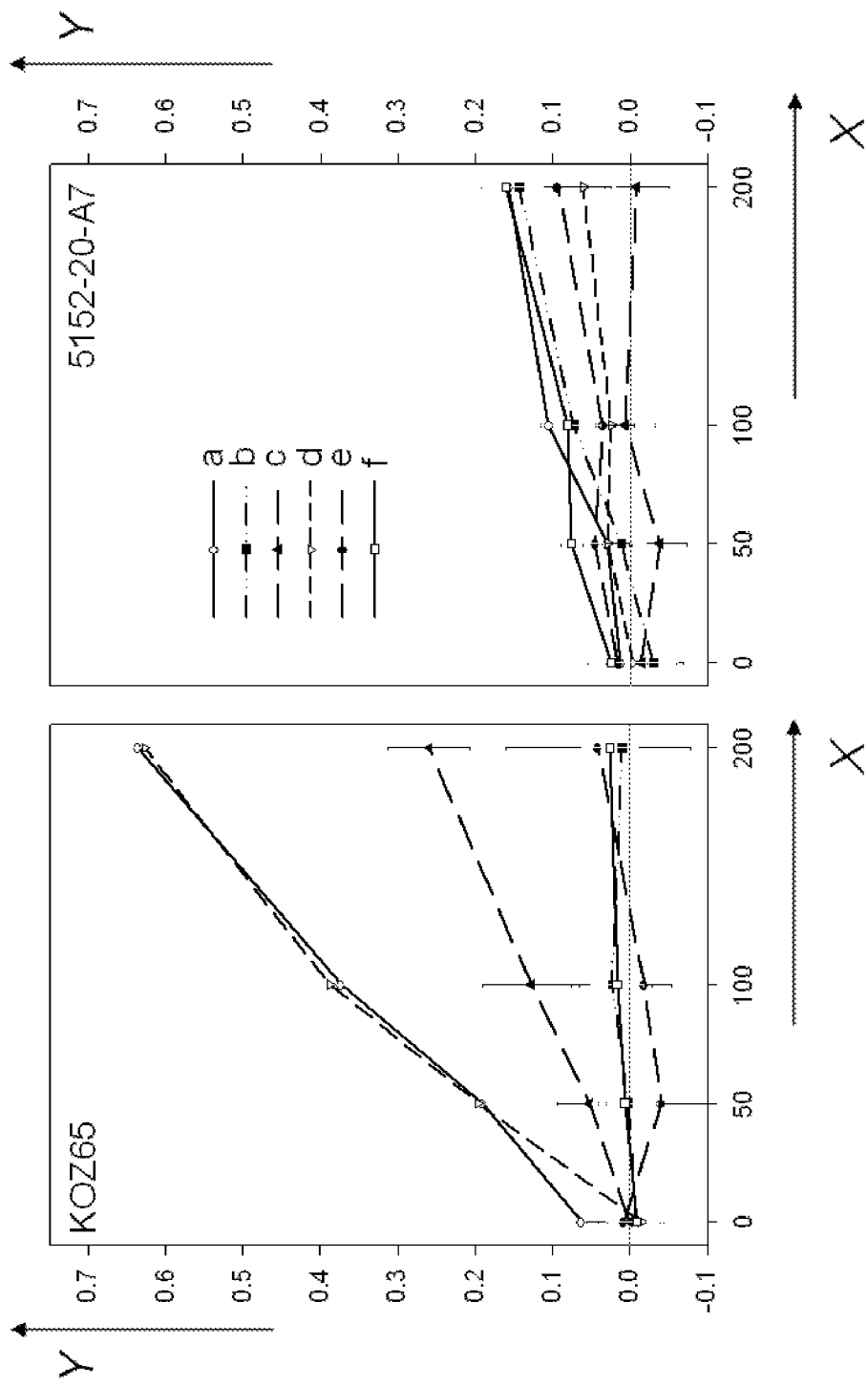

In order to draw a direct comparison between the sPQQGDH without insertion mutation from KOZ65, cleaned-up variant sPQQGDH from clone 5152-20-A7 and cleaned-up enzyme from KOZ65 were investigated on mixtures of glucose and the sugars maltose, galactose, xylose, lactose, cellobiose, or mannose. For each measurement point, quadruplicates were recorded. FIG. 6 shows that the strong interference by maltose, cellobiose, and lactose with the original enzyme from KOZ65 is suppressed in the enzyme expressed by variant 5152-20-A7. More particularly, the interference with maltose at about equimolar amounts (100 mg/dL glucose with 200 mg/dL maltose) has declined from 63% with KOZ65 to 6% with 5152-20-A7; with lactose, the interference is no longer significant.

Example 11

Comparison of Variants from Different Libraries

In order to show the general validity of the procedure according to the invention for producing sPQQGDH variants having improved substrate specificity, libraries having three, four, and five additional amino acids between positions Q168 and L169 of the wild-type sPQQGDH from KOZ65 were set up and investigated, as described in the preceding examples. For comparison, a library having only two additional amino acids between positions Q168 and L169 was also set up and investigated. However, only ten clones having a slight improvement in substrate specificity were found (ratio of the activities on maltose and glucose between 25 and 75%). Only one clone (5156-13-G12; see table 4) had an increased substrate specificity, but with poor specific activity on glucose. As apparent from table 4 below, all libraries having three to five additional amino acids contained, however, clones which exhibit a distinctly higher substrate specificity than the wild type.

TABLE 4

| Clone | Sequence of insertion | Specific activity [U/mg] | Ratio of M/G at 30 mM | Interference (5 mM glucose/ 5 mM inhibitor) | | |
|---|---|---|---|---|---|---|
| | | | | Maltose | Galactose | Xylose |
| wt-GDH KOZ65 | — | 3000 | 90.0 | 63 | 5 | 5 |
| 5156-13-G12 | NG | 43 | 20.2 | n.d. | n.d. | n.d. |
| 5145-17-E10 | AYQ | 240 | 7.4 | −5.8 | n.d. | n.d. |
| 5145-20-E7 | AWL | 131 | 10.5 | −4 | n.d. | n.d. |
| 5146-08-E9 | AFV | 236 | 6.5 | −4.7 | n.d. | n.d. |
| 5146-10-E4 | GYI | 351 | 5.9 | −9.9 | n.d. | n.d. |
| 5181-01-C12 | GYV | 680 | 6.2 | −24.6 | n.d. | n.d. |
| 5181-02-E2 | AFI | 753 | 6.2 | −30.6 | n.d. | n.d. |
| 5181-09-G12 | AYV | 738 | 5.4 | −10.8 | n.d. | n.d. |
| 5181-13-A12 | AFQ | 188 | 13.7 | −15.7 | n.d. | n.d. |
| 5138-11-A2 | AGRM | 101 | 9.5 | 15.5 | n.d. | n.d. |
| 5138-13-D10 | GDRW | 338 | 10.6 | n.d. | n.d. | n.d. |
| 5152-21-E1 | GLAV | 166 | 11.7 | −20.7 | n.d. | n.d. |
| 5151-01-D4 | MSAKG | 149 | 13.4 | 20.9 | n.d. | n.d. |
| 5151-09-C11 | LSGKR | 41 | 15.7 | 14.5 | n.d. | n.d. |
| 5151-09-G5 | QSRGS | 78 | 13.3 | 16.2 | n.d. | n.d. |
| 5151-18-B10 | FGGTY | 108 | 17.1 | 32.2 | n.d. | n.d. |
| 5152-20-A7 | MGRFL | 530 | 7.95 | 5.6 | 17 | 15 |
| 5381-01-A2 | ASRIN | n.d. | 26.8 | 9.5 | n.d. | n.d. |
| 5381-01-F8 | AGRSN | n.d. | 17.4 | 4.4 | n.d. | n.d. |
| 5381-01-F9 | SGRIF | n.d. | 10.8 | 7.7 | n.d. | n.d. |
| 5381-03-C5 | AARYN | 208 | 20.5 | 17.1 | 17 | 19 |
| 5381-04-B6 | SGTTI | n.d. | 14.1 | 7.1 | n.d. | n.d. |
| 5381-04-C7 | AGKFH | n.d. | 17.2 | 4.8 | n.d. | n.d. |
| 5381-04-F3 | TGRIY | n.d. | 8.9 | 8.6 | n.d. | n.d. |
| 5381-05-C4 | VSTFF | 264 | 9.5 | 1.2 | 6 | 1 |
| 5381-06-C12 | VSKNH | 229 | 10 | 3.8 | 13 | 7 |
| 5381-07-F10 | SSRNH | 203 | 9.5 | 4.2 | 14 | 13 |
| 5381-07-G12 | ASKFH | n.d. | 16.1 | 10.5 | n.d. | n.d. |
| 5381-08-C1 | ASKNN | 299 | 15.9 | 10.9 | 19 | 7 |
| 5381-08-F4 | TGRIL | n.d. | 7.3 | 5.3 | n.d. | n.d. |
| 5381-08-H8 | AGRIN | n.d. | 13.1 | 6.5 | n.d. | n.d. |
| 5381-09-A11 | SGRIL | 411 | 6.6 | 5.3 | 13 | 13 |
| 5381-11-H8 | SGKYH | 255 | 13.5 | 6.3 | 19 | 13 |
| 5386-05-C4 | MGRYN | 163 | 8.8 | 10.8 | 15 | 4 |
| 5386-08-D10 | VGRLT | 272 | 6.4 | 5.7 | 17 | 1 |
| 5386-11-A7 | TGRFN | 177 | 11.3 | 5.4 | 18 | 4 |
| 5386-13-F10 | AERNY | 110 | 7.6 | 0.2 | −3 | −4 |

TABLE 4-continued

| Clone | Sequence of insertion | Specific activity [U/mg] | Ratio of M/G at 30 mM | Interference (5 mM glucose/ 5 mM inhibitor) | | |
|---|---|---|---|---|---|---|
| | | | | Maltose | Galactose | Xylose |
| 5386-19-B9 | MESHN | 111 | 8.2 | 7.8 | 3 | 4 |
| 5388-15-G8 | VGHVT | 296 | 6.2 | 3.8 | 26 | 8 |
| 5388-19-F3 | VGRYQ | 188 | 7.3 | 4.8 | 16 | 14 |

(n.d.: not determined)

FIG. 1 shows the production of a vector for the insertion of synthetic DNA fragments. The positions and orientations (thick, black arrows in 1b) of the primers for producing two fragments (PCR 1, PCR 2) from the sPQQGDH gene from KOZ65 (1a) and the site to which additional amino acids are to be added later ("IP" in 1a and 1b) are shown. FIG. 1c shows schematically the assembly of the vector pAI3B-KOZ65-U (1-2) from the amplicon from the upper part of the coding sequence which has been cut with XbaI and EcoO109I and cleaned up, the amplicon from the middle part of the coding sequence which has been cut with EcoO109I and BfuAI and cleaned up, and the 3567 bp long vector fragment which has been cut with XbaI and BfuAI from the original vector pAI3B-KOZ65 (1-1) and cleaned up. The completed vector pAI3B-KOZ65-U (1-2) is displayed in FIG. 1e. From FIG. 1d, it can be see that the translation of sPQQGDH in pAI3B-KOZ65-U stops four amino acid residues after the EcoO109I restriction site when no insertion takes place.

FIG. 2 shows the production of a synthetic, double-standed piece of DNA from the oligonucleotides described in the text (displayed in the figure as arrows; the arrow head indicates in each case the 3' end of the sequence). In the lower part, the oligonucleotides EarV2-Random and EarV2-Lower are displayed. In the first step, the 62 bp long primary product is created from these overlapping single strands. Produced from it in the second step with the help of the oligonucleotides EarV2-UpAmp and EarV2-LoAmp is the 97 bp long PCR product, of which the DNA sequence is displayed in the upper part. The protein sequence encoded by it is to be found at the lower edge of FIG. 2. In the DNA sequence, the location of both EarI restriction sites is displayed. The 64 bp long fragment released with EarI from the PCR product is ligated into the vector opened with EcoO109I.

FIG. 3 shows the summary of the data from the screening of a library of variant sPQQGDH clones using the example of two microtiter plates (a and b). The abscissa (X-axis) gives for each colony of a MTP the approximate rate, in arbitrary relative units, at which glucose is converted by this colony. On the ordinate (Y-axis), the quotient from maltose conversion and glucose conversion is plotted. This makes it possible to estimate for each colony whether the colony is capable of converting glucose and, if so, whether the colony allows a better differentiation of glucose and maltose than the wild type KOZ65. To symbolize each colony, its position on the respective microtiter plate was used, A1-H12. The positive control KOZ65 is indicated with arrows.

FIG. 4 shows the results of the colonies selected from the screening described in example 3. Three parameters are considered: the conversion rate on glucose, not displayed in this picture, should be as high as possible; the interference plotted on the abscissa (X-axis) (here, maltose is the interfering sugar) should, as should also the ratio of maltose conversion to glucose conversion plotted on the ordinate (Y-axis), be as close to zero as possible. For comparison, a number of clones in FIGS. 3 and 4 are marked in the same way.

FIG. 5 shows interference studies of various clones with maltose (a), galactose (b), and xylose (c). The behavior toward mixtures of glucose and three other sugars is shown for five cleaned-up variant sPQQGDH preparations. Plotted on the ordinate (Y-axis) are the interference ascertained for mixtures of 100 mg/dL glucose in the starting measurement solution without further sugars and also with 50, 100, 150, 200, or 250 mg/dL (X-axis) of the respective interfering sugar. Each measurement point was determined as a quadruplicate.

FIG. 6 shows interference studies for KOZ65 (left) and clone 5152-20-A7 (right) on various sugars. For cellobiose (a), galactose (b), lactose (c), maltose (d), mannose (e), and xylose (f), it is plotted on the ordinate (Y-axis) how strongly these sugars, at various concentrations, affect the activity of the sPQQGDH from KOZ65 or 5152-20-A7 in the presence of 100 mg/dL glucose (inhibitor concentration [mg/dL] on the X-axis). Each measurement series for an interfering sugar also includes a measurement without this sugar, and this measurement, like all other measurements of the series, was based on a glucose value averaged from all measurements without interfering sugar. Owing to measurement inaccuracy with enzymatic tests, the individual graphs accordingly do not necessarily start at zero, as should theoretically be the case.

The invention claimed is:

1. A soluble pyrroloquinoline-quinone-dependent glucose dehydrogenase (sPQQGDH), comprising the amino acid sequence of SEQ ID NO: 22, having, compared with the sPQQGDH wild-type strain LMD 79.41 from *Acinetobacter calcoaceticus*, an insertion of three to five amino acids between positions Q168 and L169 wherein said insertion is selected from the group consisting of:

(a) an insertion of 3 amino acids, wherein the inserted amino acids have an A or G at position 1, a Y, F, or W at position 2, and a Q, L, V, or I at position 3, (b) an insertion of 4 amino acids, wherein the inserted amino acids have an A or G at position 1, a G, D, or L at position 2, an R or A at position 3, and an M or V at position 4, and (c) an insertion of 5 amino acids, wherein the inserted amino acids have an A, M, S, or V at position 1, an E, G, or S at position 2, an H, K, R, S, or T at position 3, an F, H, I, L, N, V or Y at position 4, and an F, H, L, N, Q, T, or Y at position 5.

2. The sPQQGDH as claimed in claim 1, which arises by mutagenesis from a strain selected from the group consisting of PT16, KOZ62, KOZ65, PTN69, KG106, PTN26, PT15, KGN80, KG140, KGN34, KGN25, and KGN 100.

3. The sPQQGDH as claimed in claim 1, having an insertion sequence from the group consisting of sequences SEQ ID 1 to SEQ ID 18.

4. A gene which encodes one of the proteins as claimed in claim 1.

5. A vector, having, in the region of the insertion site, a unique restriction site so that oligonucleotide sequences which encode an sPQQGDH as claimed in claim 1 can be inserted at this site.

6. The vector as claimed in claim 5 having the sequence SEQ ID 27.

7. A method for producing and identifying sPQQGDHs as claimed in claim 1, said method comprising producing a vector having a unique restriction site in the region of the insertion site in a first step, inserting a multiplicity of different oligonucleotide sequences into the vector in a second step, transforming the recombinant vectors thus obtained into host bacteria and the bacteria are propagated in a third step, screening the sPQQGDHs produced by the bacteria in a fourth step such that both the individual activities of the sPQQGDH on at least two different sugars and the interference of at least one sugar with at least one other one are determined, and selecting those sPQQGDHs which have an improved substrate specificity over the unmodified sPQQGDH of the wild strain in a fifth step.

8. A glucose sensor comprising an sPQQGDH of claim 1.

* * * * *

SEQUENCE LISTING

```
<160> NUMBER OF SEQ ID NOS: 35

<210> SEQ ID NO 1
<211> LENGTH: 3
<212> TYPE: PRT
<213> ORGANISM: Artificial
<220> FEATURE:
<223> OTHER INFORMATION: Synthetized sPQQGDH KOZ65 variant sequence

<400> SEQUENCE: 1

Ala Tyr Gln
1

<210> SEQ ID NO 2
<211> LENGTH: 3
<212> TYPE: PRT
<213> ORGANISM: Artificial
<220> FEATURE:
<223> OTHER INFORMATION: Synthetized sPQQGDH KOZ65 variant sequence

<400> SEQUENCE: 2

Ala Trp Leu
1

<210> SEQ ID NO 3
<211> LENGTH: 3
<212> TYPE: PRT
<213> ORGANISM: Artificial
<220> FEATURE:
<223> OTHER INFORMATION: Synthetized sPQQGDH KOZ65 variant sequence

<400> SEQUENCE: 3

Ala Phe Val
1

<210> SEQ ID NO 4
<211> LENGTH: 3
<212> TYPE: PRT
<213> ORGANISM: Artificial
<220> FEATURE:
<223> OTHER INFORMATION: Synthetized sPQQGDH KOZ65 variant sequence

<400> SEQUENCE: 4

Gly Tyr Ile
1

<210> SEQ ID NO 5
<211> LENGTH: 3
<212> TYPE: PRT
<213> ORGANISM: Artificial
<220> FEATURE:
```

```
<223> OTHER INFORMATION: Synthetized sPQQGDH KOZ65 variant sequence

<400> SEQUENCE: 5

Ala Tyr Val
1

<210> SEQ ID NO 6
<211> LENGTH: 3
<212> TYPE: PRT
<213> ORGANISM: Artificial
<220> FEATURE:
<223> OTHER INFORMATION: Synthetized sPQQGDH KOZ65 variant sequence

<400> SEQUENCE: 6

Ala Phe Gln
1

<210> SEQ ID NO 7
<211> LENGTH: 4
<212> TYPE: PRT
<213> ORGANISM: Artificial
<220> FEATURE:
<223> OTHER INFORMATION: Synthetized sPQQGDH KOZ65 variant sequence

<400> SEQUENCE: 7

Ala Gly Arg Met
1

<210> SEQ ID NO 8
<211> LENGTH: 4
<212> TYPE: PRT
<213> ORGANISM: Artificial
<220> FEATURE:
<223> OTHER INFORMATION: Synthetized sPQQGDH KOZ65 variant sequence

<400> SEQUENCE: 8

Gly Leu Ala Val
1

<210> SEQ ID NO 9
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 9

Met Gly Arg Phe Leu
1               5

<210> SEQ ID NO 10
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 10

Val Ser Thr Phe Phe
1               5

<210> SEQ ID NO 11
<211> LENGTH: 5
<212> TYPE: PRT
<213> ORGANISM: Artificial
<220> FEATURE:
<223> OTHER INFORMATION: Synthetized sPQQGDH KOZ65 variant sequence
```

```
<400> SEQUENCE: 11

Val Ser Lys Asn His
1               5

<210> SEQ ID NO 12
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 12

Ser Ser Arg Asn His
1               5

<210> SEQ ID NO 13
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 13

Ser Gly Arg Ile Leu
1               5

<210> SEQ ID NO 14
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 14

Val Gly Arg Leu Thr
1               5

<210> SEQ ID NO 15
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 15

Ala Glu Arg Asn Tyr
1               5

<210> SEQ ID NO 16
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 16

Met Glu Ser His Asn
1               5

<210> SEQ ID NO 17
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 17
```

-continued

Val Gly His Val Thr
1               5

<210> SEQ ID NO 18
<211> LENGTH: 5
<212> TYPE: PRT
<213> ORGANISM: Artificial
<220> FEATURE:
<223> OTHER INFORMATION: Synthetized sPQQGDH KOZ65 variant sequence

<400> SEQUENCE: 18

Val Gly Arg Tyr Gln
1               5

<210> SEQ ID NO 19
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 19
tggtaggtct caaatgaata aacatttatt ggctaaaatt ac                              42

<210> SEQ ID NO 20
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 20
ttcagctctg agctttatat gtaaatctaa tc                                         32

<210> SEQ ID NO 21
<211> LENGTH: 4560
<212> TYPE: DNA
<213> ORGANISM: Artificial
<220> FEATURE:
<223> OTHER INFORMATION: Synthetic expression plasmid
<220> FEATURE:
<221> NAME/KEY: CDS
<222> LOCATION: (139)..(1581)
<220> FEATURE:
<221> NAME/KEY: sig_peptide
<222> LOCATION: (139)..(213)
<220> FEATURE:
<221> NAME/KEY: mat_peptide
<222> LOCATION: (214)..(1581)

<400> SEQUENCE: 21
ccatcgaatg gccagatgat taattcctaa tttttgttga cactctatca ttgatagagt           60
tattttacca ctccctatca gtgatagaga aaagtgaaat gaatagttcg acaaaaatct          120
agataacgag ggcaaaaa atg aat aaa cat tta ttg gct aaa att act tta            171
                    Met Asn Lys His Leu Leu Ala Lys Ile Thr Leu
                     -25             -20                 -15 tta ggt gct gct cag cta ctt acg ctc aat tca gca ttt gct gat gtc            219
Leu Gly Ala Ala Gln Leu Leu Thr Leu Asn Ser Ala Phe Ala Asp Val
            -10                 -5                 -1  1 cct ctt aca cca tct caa ttt gct aaa gcg aaa aca gaa agc ttt gat            267
Pro Leu Thr Pro Ser Gln Phe Ala Lys Ala Lys Thr Glu Ser Phe Asp
         5                  10                  15 aag aaa gtt ctt cta tct aat tta aat aag cca cat gct ttg ttg tgg            315
Lys Lys Val Leu Leu Ser Asn Leu Asn Lys Pro His Ala Leu Leu Trp
    20                  25                  30 gga ccg gat aat caa att tgg tta acg gag cgg gca aca ggt aag att            363

```
                Gly Pro Asp Asn Gln Ile Trp Leu Thr Glu Arg Ala Thr Gly Lys Ile
                 35                  40                  45                  50 cta aga gtt aat cca gag tcg ggc agt gta aaa aca gtt ttt cag gtt        411
Leu Arg Val Asn Pro Glu Ser Gly Ser Val Lys Thr Val Phe Gln Val
                         55                  60                  65 cct gag att gta aat gat gct gat gga caa aac ggt tta ttg ggt ttt        459
Pro Glu Ile Val Asn Asp Ala Asp Gly Gln Asn Gly Leu Leu Gly Phe
                 70                  75                  80 gcc ttt cat cct gac ttt aaa aat aat cct tat atc tat gtt tca ggt        507
Ala Phe His Pro Asp Phe Lys Asn Asn Pro Tyr Ile Tyr Val Ser Gly
             85                  90                  95 aca ttt aaa aat ccg aaa tct aca gat aaa gaa tta ccg aat caa act        555
Thr Phe Lys Asn Pro Lys Ser Thr Asp Lys Glu Leu Pro Asn Gln Thr
        100                 105                 110 att atc cgt cga tat acc tat aac aag gca aca gat acc ctt gag aaa        603
Ile Ile Arg Arg Tyr Thr Tyr Asn Lys Ala Thr Asp Thr Leu Glu Lys
    115                 120                 125                 130 cca gta gat tta ttg gca gga tta cct tca tcg aaa gac cat cag tcg        651
Pro Val Asp Leu Leu Ala Gly Leu Pro Ser Ser Lys Asp His Gln Ser
                135                 140                 145 ggt cgt ctt gtg att ggt cca gac caa aag att tac tat acg att ggt        699
Gly Arg Leu Val Ile Gly Pro Asp Gln Lys Ile Tyr Tyr Thr Ile Gly
            150                 155                 160 gat cag gga cgt aac cag ctg gct tat tta ttc tta cca aat caa gca        747
Asp Gln Gly Arg Asn Gln Leu Ala Tyr Leu Phe Leu Pro Asn Gln Ala
        165                 170                 175 cag cat acg ccg act caa cag gaa ctg agc ggc aaa gac tat cat acc        795
Gln His Thr Pro Thr Gln Gln Glu Leu Ser Gly Lys Asp Tyr His Thr
    180                 185                 190 tat atg ggt aaa gta ttg cgc tta aat ctg gat gga agt att cca aaa        843
Tyr Met Gly Lys Val Leu Arg Leu Asn Leu Asp Gly Ser Ile Pro Lys
195                 200                 205                 210 gat aat cca agc ttt aac ggt gta att agc cat att tat acg ctc ggt        891
Asp Asn Pro Ser Phe Asn Gly Val Ile Ser His Ile Tyr Thr Leu Gly
                215                 220                 225 cat cgt aac cca cag ggc ttg gca ttt act cca aat ggt aaa ctg ttg        939
His Arg Asn Pro Gln Gly Leu Ala Phe Thr Pro Asn Gly Lys Leu Leu
            230                 235                 240 caa tct gaa cag ggt cca aac tct gat gat gaa att aac ctc att gtc        987
Gln Ser Glu Gln Gly Pro Asn Ser Asp Asp Glu Ile Asn Leu Ile Val
        245                 250                 255 aaa ggt ggt aac tat ggc tgg cca aat gta gcg ggt tat aaa gat gat       1035
Lys Gly Gly Asn Tyr Gly Trp Pro Asn Val Ala Gly Tyr Lys Asp Asp
    260                 265                 270 agt ggt tat gcc tat gca aat tat tcg gca gca agc aat aaa gca caa       1083
Ser Gly Tyr Ala Tyr Ala Asn Tyr Ser Ala Ala Ser Asn Lys Ala Gln
275                 280                 285                 290 att aaa gat tta gga caa aat ggt tta aaa gtg gcg gca ggt gta cct       1131
Ile Lys Asp Leu Gly Gln Asn Gly Leu Lys Val Ala Ala Gly Val Pro
                295                 300                 305 gtg atg aaa gag tct gaa tgg act ggt aaa aac ttt gta ccg ccg tta       1179
Val Met Lys Glu Ser Glu Trp Thr Gly Lys Asn Phe Val Pro Pro Leu
            310                 315                 320 aaa act tta tat acc gtc caa gat acc tat aac tat aat gac cca act       1227
Lys Thr Leu Tyr Thr Val Gln Asp Thr Tyr Asn Tyr Asn Asp Pro Thr
        325                 330                 335 tgt ggg gat atg acc tac att tgc tgg cca acg gtt gcg ccg tca tct       1275
Cys Gly Asp Met Thr Tyr Ile Cys Trp Pro Thr Val Ala Pro Ser Ser
    340                 345                 350 gct tat gtc tat aag gga ggc aaa aaa gca att tct ggt tgg gaa aat       1323
```

|   |   |   |   |   |   |   |   |   |   |   |   |   |   |   |   |
|---|---|---|---|---|---|---|---|---|---|---|---|---|---|---|---|
| Ala | Tyr | Val | Tyr | Lys | Gly | Gly | Lys | Lys | Ala | Ile | Ser | Gly | Trp | Glu | Asn |
| 355 |   |   |   |   | 360 |   |   |   | 365 |   |   |   |   | 370 |   |

```
aca  tta  ttg  gtt  cca  tct  tta  aag  cgc  ggt  gtt  att  ttc  cgt  att  aag     1371
Thr  Leu  Leu  Val  Pro  Ser  Leu  Lys  Arg  Gly  Val  Ile  Phe  Arg  Ile  Lys
                    375                      380                      385 cta  gat  cca  act  tac  agt  act  act  tat  gat  gat  gct  gtg  ccg  atg  ttt     1419
Leu  Asp  Pro  Thr  Tyr  Ser  Thr  Thr  Tyr  Asp  Asp  Ala  Val  Pro  Met  Phe
               390                      395                      400 aag  agc  aac  aat  cgt  tat  cgt  gac  gtg  att  gca  agt  cca  gat  ggg  aat     1467
Lys  Ser  Asn  Asn  Arg  Tyr  Arg  Asp  Val  Ile  Ala  Ser  Pro  Asp  Gly  Asn
               405                      410                      415 gtt  tta  tat  gta  ttg  act  gat  act  tcc  gga  aat  gtc  caa  aaa  gat  gat     1515
Val  Leu  Tyr  Val  Leu  Thr  Asp  Thr  Ser  Gly  Asn  Val  Gln  Lys  Asp  Asp
               420                      425                      430 ggt  tct  gta  acg  aat  aca  tta  gaa  aac  cca  gga  tct  ctg  att  aga  ttt     1563
Gly  Ser  Val  Thr  Asn  Thr  Leu  Glu  Asn  Pro  Gly  Ser  Leu  Ile  Arg  Phe
435            440                      445                      450 aca  tat  aaa  gct  cag  agc  tgaaagcttg acctgtgaag tgaaaatgg                       1611
Thr  Tyr  Lys  Ala  Gln  Ser
                    455
```

| | |
|---|---|
| cgcacattgt gcgacatttt ttttgtctgc cgtttaccgc tactgcgtca cggatctcca | 1671 |
| cgcgccctgt agcggcgcat taagcgcggc gggtgtggtg gttacgcgca gcgtgaccgc | 1731 |
| tacacttgcc agcgccctag cgcccgctcc tttcgctttc ttcccttcct ttctcgccac | 1791 |
| gttcgccggc tttccccgtc aagctctaaa tcggggctc cctttagggt tccgatttag | 1851 |
| tgctttacgg cacctcgacc ccaaaaaact tgattaggt gatggttcac gtagtgggcc | 1911 |
| atcgccctga tagacggttt ttcgcccttt gacgttggag tccacgttct taatagtgg | 1971 |
| actcttgttc caaactggaa caacactcaa ccctatctcg gtctattctt ttgatttata | 2031 |
| agggattttg ccgatttcgg cctattggtt aaaaaatgag ctgatttaac aaaaatttaa | 2091 |
| cgcgaatttt aacaaaatat taacgcttac aatttcaggt ggcactttc ggggaaatgt | 2151 |
| gcgcggaacc cctatttgtt tattttcta aatacattca aatatgtatc cgctcatgag | 2211 |
| acaataaccc tgataaatgc ttcaataata ttgaaaaagg aagagtatga gtattcaaca | 2271 |
| tttccgtgtc gcccttattc cctttttgc ggcattttgc cttcctgttt ttgctcaccc | 2331 |
| agaaacgctg gtgaaagtaa aagatgctga agatcagttg ggtgcacgag tgggttacat | 2391 |
| cgaactggat ctcaacagcg gtaagatcct tgagagtttt cgccccgaag aacgttttcc | 2451 |
| aatgatgagc acttttaaag ttctgctatg tggcgcggta ttatcccgta ttgacgccgg | 2511 |
| gcaagagcaa ctcggtcgcc gcatacacta ttctcagaat gacttggttg agtactcacc | 2571 |
| agtcacagaa aagcatctta cggatggcat gacagtaaga gaattatgca gtgctgccat | 2631 |
| aaccatgagt gataacactg cggccaactt acttctgaca acgatcggag gaccgaagga | 2691 |
| gctaaccgct tttttgcaca acatggggga tcatgtaact cgccttgatc gttgggaacc | 2751 |
| ggagctgaat gaagccatac caaacgacga gcgtgacacc acgatgcctg tagcaatggc | 2811 |
| aacaacgttg cgcaaactat taactggcga actacttact ctagcttccc ggcaacaatt | 2871 |
| gatagactgg atggaggcgg ataaagttgc aggaccactt ctgcgctcgg cccttccggc | 2931 |
| tggctggttt attgctgata atctggagc cggtgagcgt ggctctcgcg gtatcattgc | 2991 |
| agcactgggg ccagatggta agccctcccg tatcgtagtt atctacacga cggggagtca | 3051 |
| ggcaactatg gatgaacgaa atagacagat cgctgagata ggtgcctcac tgattaagca | 3111 |
| ttggtaggaa ttaatgatgt ctcgtttaga taaaagtaaa gtgattaaca gcgcattaga | 3171 |
| gctgcttaat gaggtcggaa tcgaaggttt aacaacccgt aaactcgccc agaagctagg | 3231 |

```
tgtagagcag cctacattgt attggcatgt aaaaaataag cgggctttgc tcgacgcctt    3291
agccattgag atgttagata ggcaccatac tcactttgc cctttagaag gggaaagctg    3351
gcaagatttt ttacgtaata acgctaaaag ttttagatgt gctttactaa gtcatcgcga    3411
tggagcaaaa gtacatttag gtacacggcc tacagaaaaa cagtatgaaa ctctcgaaaa    3471
tcaattagcc ttttatgcc aacaaggttt tcactagag aatgcattat atgcactcag    3531
cgcagtgggg cattttactt taggttgcgt attggaagat caagagcatc aagtcgctaa    3591
agaagaaagg gaaacaccta ctactgatag tatgccgcca ttattacgac aagctatcga    3651
attatttgat caccaaggtg cagagccagc cttcttattc ggccttgaat tgatcatatg    3711
cggattagaa aaacaactta aatgtgaaag tgggtcttaa aagcagcata accttttcc    3771 gtgatggtaa cttcactagt ttaaaaggat ctaggtgaag atccttttg ataatctcat    3831 gaccaaaatc ccttaacgtg agttttcgtt ccactgagcg tcagaccccg tagaaaagat    3891
caaaggatct tcttgagatc cttttttct gcgcgtaatc tgctgcttgc aaacaaaaaa    3951
accaccgcta ccagcggtgg tttgtttgcc ggatcaagag ctaccaactc tttttccgaa    4011
ggtaactggc ttcagcagag cgcagatacc aaatactgtc cttctagtgt agccgtagtt    4071
aggccaccac ttcaagaact ctgtagcacc gcctacatac ctcgctctgc taatcctgtt    4131
accagtggct gctgccagtg gcgataagtc gtgtcttacc gggttggact caagacgata    4191
gttaccggat aaggcgcagc ggtcgggctg aacggggggt tcgtgcacac agcccagctt    4251
ggagcgaacg acctacaccg aactgagata cctacagcgt gagctatgag aaagcgccac    4311
gcttcccgaa gggagaaagg cggacaggta tccggtaagc ggcagggtcg aacaggaga    4371 gcgcacgagg gagcttccag ggggaaacgc ctggtatctt tatagtcctg tcgggtttcg    4431
ccacctctga cttgagcgtc gatttttgtg atgctcgtca ggggggcgga gcctatggaa    4491
aaacgccagc aacgcggcct ttttacggtt cctggccttt tgctggcctt ttgctcacat    4551
gacccgaca                                                            4560
```

<210> SEQ ID NO 22
<211> LENGTH: 481
<212> TYPE: PRT
<213> ORGANISM: Artificial
<220> FEATURE:
<223> OTHER INFORMATION: Synthetic Construct

<400> SEQUENCE: 22

```
Met Asn Lys His Leu Leu Ala Lys Ile Thr Leu Gly Ala Ala Gln
-25                 -20                 -15                 -10

Leu Leu Thr Leu Asn Ser Ala Phe Ala Asp Val Pro Leu Thr Pro Ser
                -5                  -1   1               5

Gln Phe Ala Lys Ala Lys Thr Glu Ser Phe Asp Lys Lys Val Leu Leu
            10                  15                  20

Ser Asn Leu Asn Lys Pro His Ala Leu Leu Trp Gly Pro Asp Asn Gln
            25                  30                  35

Ile Trp Leu Thr Glu Arg Ala Thr Gly Lys Ile Leu Arg Val Asn Pro
40                  45                  50                  55

Glu Ser Gly Ser Val Lys Thr Val Phe Gln Val Pro Glu Ile Val Asn
                60                  65                  70

Asp Ala Asp Gly Gln Asn Gly Leu Leu Gly Phe Ala Phe His Pro Asp
            75                  80                  85

Phe Lys Asn Asn Pro Tyr Ile Tyr Val Ser Gly Thr Phe Lys Asn Pro
            90                  95                  100
```

```
Lys Ser Thr Asp Lys Glu Leu Pro Asn Gln Thr Ile Ile Arg Arg Tyr
    105                 110                 115
Thr Tyr Asn Lys Ala Thr Asp Thr Leu Glu Lys Pro Val Asp Leu Leu
120                 125                 130                 135
Ala Gly Leu Pro Ser Ser Lys Asp His Gln Ser Gly Arg Leu Val Ile
                140                 145                 150
Gly Pro Asp Gln Lys Ile Tyr Tyr Thr Ile Gly Asp Gln Gly Arg Asn
                155                 160                 165
Gln Leu Ala Tyr Leu Phe Leu Pro Asn Gln Ala Gln His Thr Pro Thr
            170                 175                 180
Gln Gln Glu Leu Ser Gly Lys Asp Tyr His Thr Tyr Met Gly Lys Val
        185                 190                 195
Leu Arg Leu Asn Leu Asp Gly Ser Ile Pro Lys Asp Asn Pro Ser Phe
200                 205                 210                 215
Asn Gly Val Ile Ser His Ile Tyr Thr Leu Gly His Arg Asn Pro Gln
                220                 225                 230
Gly Leu Ala Phe Thr Pro Asn Gly Lys Leu Leu Gln Ser Glu Gln Gly
                235                 240                 245
Pro Asn Ser Asp Asp Glu Ile Asn Leu Ile Val Lys Gly Gly Asn Tyr
            250                 255                 260
Gly Trp Pro Asn Val Ala Gly Tyr Lys Asp Asp Ser Gly Tyr Ala Tyr
        265                 270                 275
Ala Asn Tyr Ser Ala Ala Ser Asn Lys Ala Gln Ile Lys Asp Leu Gly
280                 285                 290                 295
Gln Asn Gly Leu Lys Val Ala Ala Gly Val Pro Val Met Lys Glu Ser
                300                 305                 310
Glu Trp Thr Gly Lys Asn Phe Val Pro Pro Leu Lys Thr Leu Tyr Thr
                315                 320                 325
Val Gln Asp Thr Tyr Asn Tyr Asn Asp Pro Thr Cys Gly Asp Met Thr
            330                 335                 340
Tyr Ile Cys Trp Pro Thr Val Ala Pro Ser Ser Ala Tyr Val Tyr Lys
        345                 350                 355
Gly Gly Lys Lys Ala Ile Ser Gly Trp Glu Asn Thr Leu Leu Val Pro
360                 365                 370                 375
Ser Leu Lys Arg Gly Val Ile Phe Arg Ile Lys Leu Asp Pro Thr Tyr
                380                 385                 390
Ser Thr Thr Tyr Asp Asp Ala Val Pro Met Phe Lys Ser Asn Asn Arg
                395                 400                 405
Tyr Arg Asp Val Ile Ala Ser Pro Asp Gly Asn Val Leu Tyr Val Leu
            410                 415                 420
Thr Asp Thr Ser Gly Asn Val Gln Lys Asp Asp Gly Ser Val Thr Asn
        425                 430                 435
Thr Leu Glu Asn Pro Gly Ser Leu Ile Arg Phe Thr Tyr Lys Ala Gln
440                 445                 450                 455
Ser

<210> SEQ ID NO 23
<211> LENGTH: 22
<212> TYPE: DNA
<213> ORGANISM: Artificial
<220> FEATURE:
<223> OTHER INFORMATION: Synthetic PCR-primer

<400> SEQUENCE: 23
tagagttatt ttaccactcc ct                                          22
```

<210> SEQ ID NO 24
<211> LENGTH: 24
<212> TYPE: DNA
<213> ORGANISM: Artificial
<220> FEATURE:
<223> OTHER INFORMATION: Synthetic PCR-primer

<400> SEQUENCE: 24
ggttaggtcc ctgatcacca atcg                                          24

<210> SEQ ID NO 25
<211> LENGTH: 22
<212> TYPE: DNA
<213> ORGANISM: Artificial
<220> FEATURE:
<223> OTHER INFORMATION: Synthetic PCR-primer

<400> SEQUENCE: 25
cacaggtaca cctgccgcca ct                                            22

<210> SEQ ID NO 26
<211> LENGTH: 25
<212> TYPE: DNA
<213> ORGANISM: Artificial
<220> FEATURE:
<223> OTHER INFORMATION: Synthetic PCR-primer

<400> SEQUENCE: 26
tacgaggacc caacaggaac tgagc                                         25

<210> SEQ ID NO 27
<211> LENGTH: 4508
<212> TYPE: DNA
<213> ORGANISM: Artificial
<220> FEATURE:
<223> OTHER INFORMATION: Synthetic expression vector
<220> FEATURE:
<221> NAME/KEY: CDS
<222> LOCATION: (139)..(720)
<220> FEATURE:
<221> NAME/KEY: sig_peptide
<222> LOCATION: (139)..(213)
<220> FEATURE:
<221> NAME/KEY: mat_peptide
<222> LOCATION: (214)..(720)

<400> SEQUENCE: 27
ccatcgaatg gccagatgat taattcctaa tttttgttga cactctatca ttgatagagt    60
tattttacca ctccctatca gtgatagaga aaagtgaaat gaatagttcg acaaaaatct   120
agataacgag ggcaaaaa atg aat aaa cat tta ttg gct aaa att act tta    171
                    Met Asn Lys His Leu Leu Ala Lys Ile Thr Leu
                        -25             -20              -15 tta ggt gct gct cag cta ctt acg ctc aat tca gca ttt gct gat gtc    219
Leu Gly Ala Ala Gln Leu Leu Thr Leu Asn Ser Ala Phe Ala Asp Val
            -10              -5              -1   1 cct ctt aca cca tct caa ttt gct aaa gcg aaa aca gaa agc ttt gat    267
Pro Leu Thr Pro Ser Gln Phe Ala Lys Ala Lys Thr Glu Ser Phe Asp
        5                  10                  15 aag aaa gtt ctt cta tct aat tta aat aag cca cat gct ttg ttg tgg    315
Lys Lys Val Leu Leu Ser Asn Leu Asn Lys Pro His Ala Leu Leu Trp
    20                  25                  30 gga ccg gat aat caa att tgg tta acg gag cgg gca aca ggt aag att    363
Gly Pro Asp Asn Gln Ile Trp Leu Thr Glu Arg Ala Thr Gly Lys Ile
35                  40                  45                  50

```
cta aga gtt aat cca gag tcg ggc agt gta aaa aca gtt ttt cag gtt      411
Leu Arg Val Asn Pro Glu Ser Gly Ser Val Lys Thr Val Phe Gln Val
             55                  60                  65 cct gag att gta aat gat gct gat gga caa aac ggt tta ttg ggt ttt      459
Pro Glu Ile Val Asn Asp Ala Asp Gly Gln Asn Gly Leu Leu Gly Phe
             70                  75                  80 gcc ttt cat cct gac ttt aaa aat aat cct tat atc tat gtt tca ggt      507
Ala Phe His Pro Asp Phe Lys Asn Asn Pro Tyr Ile Tyr Val Ser Gly
             85                  90                  95 aca ttt aaa aat ccg aaa tct aca gat aaa gaa tta ccg aat caa act      555
Thr Phe Lys Asn Pro Lys Ser Thr Asp Lys Glu Leu Pro Asn Gln Thr
            100                 105                 110 att atc cgt cga tat acc tat aac aag gca aca gat acc ctt gag aaa      603
Ile Ile Arg Arg Tyr Thr Tyr Asn Lys Ala Thr Asp Thr Leu Glu Lys
115                 120                 125                 130 cca gta gat tta ttg gca gga tta cct tca tcg aaa gac cat cag tcg      651
Pro Val Asp Leu Leu Ala Gly Leu Pro Ser Ser Lys Asp His Gln Ser
            135                 140                 145 ggt cgt ctt gtg att ggt cca gac caa aag att tac tat acg att ggt      699
Gly Arg Leu Val Ile Gly Pro Asp Gln Lys Ile Tyr Tyr Thr Ile Gly
            150                 155                 160 gat cag gga ccc aac agg aac tgagcggcaa agactatcat acctatatgg         750
Asp Gln Gly Pro Asn Arg Asn
            165 gtaaagtatt gcgctttaaat ctggatggaa gtattccaaa agataatcca agctttaacg   810 gtgtaattag ccatatttat acgctcggtc atcgtaaccc acagggcttg catttactc     870 caaatggtaa actgttgcaa tctgaacagg gtccaaactc tgatgatgaa attaacctca    930 ttgtcaaagg tggtaactat ggctggccaa atgtagcggg ttataaagat gatagtggtt    990 atgcctatgc aaattattcg gcagcaagca ataaagcaca aattaaagat ttaggacaaa   1050 atggtttaaa agtggcggca ggtgtacctg tgatgaaaga gtctgaatgg actggtaaaa   1110 actttgtacc gccgttaaaa actttatata ccgtccaaga tacctataac tataatgacc   1170 caacttgtgg ggatatgacc tacatttgct ggccaacggt tgcgccgtca tctgcttatg   1230 tctataaggg aggcaaaaaa gcaatttctg gttgggaaaa tacattattg gttccatctt   1290 taaagcgcgg tgttatttc cgtattaagc tagatccaac ttacagtact acttatgatg   1350 atgctgtgcc gatgtttaag agcaacaatc gttatcgtga cgtgattgca agtccagatg   1410 ggaatgtttt atatgtattg actgatactt ccggaaatgt ccaaaaagat gatggttctg   1470 taacgaatac attagaaaac ccaggatctc tgattagatt tacatataaa gctcagagct   1530 gaaagcttga cctgtgaagt gaaaaatggc gcacattgtg cgacatttt tttgtctgcc    1590 gtttaccgct actgcgtcac ggatctccac gcgccctgta gcggcgcatt aagcgcggcg   1650 ggtgtggtgg ttacgcgcag cgtgaccgct acacttgcca gcgccctagc gcccgctcct   1710 ttcgctttct tcccttcctt tctcgccacg ttcgccggct ttccccgtca gctctaaat    1770 cgggggctcc ctttagggtt ccgatttagt gctttacggc acctcgaccc caaaaaactt   1830 gattagggtg atggttcacg tagtgggcca tcgccctgat agacggtttt tcgcccttg    1890 acgttggagt ccacgttctt taatagtgga ctcttgttcc aaactggaac aacactcaac   1950 cctatctcgg tctattcttt tgatttataa gggattttgc cgatttcggc ctattggtta   2010 aaaaatgagc tgatttaaca aaaatttaac gcgaatttta acaaaatatt aacgcttaca   2070 atttcaggtg gcacttttcg gggaaatgtg cgcggaaccc ctatttgttt attttttctaa  2130 atacattcaa atatgtatcc gctcatgaga caataaccct gataaatgct tcaataatat   2190
```

```
tgaaaaagga agagtatgag tattcaacat ttccgtgtcg cccttattcc ctttttttgcg   2250 gcattttgcc ttcctgtttt tgctcaccca gaaacgctgg tgaaagtaaa agatgctgaa   2310
gatcagttgg gtgcacgagt gggttacatc gaactggatc tcaacagcgg taagatcctt   2370
gagagttttc gccccgaaga acgttttcca atgatgagca cttttaaagt tctgctatgt   2430
ggcgcggtat tatcccgtat tgacgccggg caagagcaac tcggtcgccg catacactat   2490
tctcagaatg acttggttga gtactcacca gtcacagaaa agcatcttac ggatggcatg   2550
acagtaagag aattatgcag tgctgccata accatgagtg ataacactgc ggccaactta   2610
cttctgacaa cgatcggagg accgaaggag ctaaccgctt ttttgcacaa catgggggat   2670
catgtaactc gccttgatcg ttgggaaccg gagctgaatg aagccatacc aaacgacgag   2730
cgtgacacca cgatgcctgt agcaatggca acaacgttgc gcaaactatt aactggcgaa   2790
ctacttactc tagcttcccg gcaacaattg atagactgga tggaggcgga taaagttgca   2850
ggaccacttc tgcgctcggc ccttccggct ggctggttta ttgctgataa atctggagcc   2910
ggtgagcgtg gctctcgcgg tatcattgca gcactggggc cagatggtaa gccctcccgt   2970
atcgtagtta tctacacgac ggggagtcag gcaactatgg atgaacgaaa tagacagatc   3030
gctgagatag gtgcctcact gattaagcat tggtaggaat aatgatgtc tcgtttagat   3090 aaaagtaaag tgattaacag cgcattagag ctgcttaatg aggtcggaat cgaaggttta   3150
acaacccgta aactcgccca gaagctaggt gtagagcagc ctacattgta ttggcatgta   3210
aaaaataagc gggctttgct cgacgcctta gccattgaga tgttagatag gcaccatact   3270
cacttttgcc ctttagaagg ggaaagctgg caagattttt tacgtaataa cgctaaaagt   3330
tttagatgtg ctttactaag tcatcgcgat ggagcaaaag tacatttagg tacacggcct   3390
acagaaaaac agtatgaaac tctcgaaaat caattagcct ttttatgcca acaaggtttt   3450
tcactagaga atgcattata tgcactcagc gcagtggggc attttacttt aggttgcgta   3510
ttggaagatc aagagcatca agtcgctaaa gaagaaaggg aaacacctac tactgatagt   3570
atgccgccat tattacgaca agctatcgaa ttatttgatc accaaggtgc agagccagcc   3630
ttcttattcg gccttgaatt gatcatatgc ggattagaaa acaacttaa atgtgaaagt   3690 gggtcttaaa agcagcataa ccttttttccg tgatggtaac ttcactagtt taaaaggatc   3750
taggtgaaga tccttttttga taatctcatg accaaaatcc cttaacgtga gttttcgttc   3810
cactgagcgt cagacccgt agaaaagatc aaaggatctt cttgagatcc ttttttttctg   3870 cgcgtaatct gctgcttgca acaaaaaaaa ccaccgctac cagcggtggt ttgtttgccg   3930
gatcaagagc taccaactct ttttccgaag gtaactggct tcagcagagc gcagatacca   3990
aatactgtcc ttctagtgta gccgtagtta ggccaccact tcaagaactc tgtagcaccg   4050
cctacatacc tcgctctgct aatcctgtta ccagtggctg ctgccagtgg cgataagtcg   4110
tgtcttaccg ggttggactc aagacgatag ttaccggata aggcgcagcg gtcgggctga   4170
acggggggtt cgtgcacaca gcccagcttg gagcgaacga cctacaccga actgagatac   4230
ctacagcgtg agctatgaga aagcgccacg cttcccgaag ggagaaaggc ggacaggtat   4290
ccggtaagcg gcagggtcgg aacaggagag cgcacgaggg agcttccagg gggaaacgcc   4350
tggtatcttt atagtcctgt cgggtttcgc cacctctgac ttgagcgtcg attttttgtga   4410 tgctcgtcag gggggcggag cctatggaaa aacgccagca acgcggcctt tttacggttc   4470
ctggcctttt gctggccttt tgctcacatg acccgaca                           4508
```

<210> SEQ ID NO 28

```
<211> LENGTH: 194
<212> TYPE: PRT
<213> ORGANISM: Artificial
<220> FEATURE:
<223> OTHER INFORMATION: Synthetic Construct

<400> SEQUENCE: 28

Met Asn Lys His Leu Leu Ala Lys Ile Thr Leu Leu Gly Ala Ala Gln
-25                 -20                 -15                 -10

Leu Leu Thr Leu Asn Ser Ala Phe Ala Asp Val Pro Leu Thr Pro Ser
                -5                  -1   1                   5

Gln Phe Ala Lys Ala Lys Thr Glu Ser Phe Asp Lys Lys Val Leu Leu
             10                  15                  20

Ser Asn Leu Asn Lys Pro His Ala Leu Leu Trp Gly Pro Asp Asn Gln
         25                  30                  35

Ile Trp Leu Thr Glu Arg Ala Thr Gly Lys Ile Leu Arg Val Asn Pro
 40                  45                  50                  55

Glu Ser Gly Ser Val Lys Thr Val Phe Gln Val Pro Glu Ile Val Asn
                 60                  65                  70

Asp Ala Asp Gly Gln Asn Gly Leu Leu Gly Phe Ala Phe His Pro Asp
                 75                  80                  85

Phe Lys Asn Asn Pro Tyr Ile Tyr Val Ser Gly Thr Phe Lys Asn Pro
             90                  95                 100

Lys Ser Thr Asp Lys Glu Leu Pro Asn Gln Thr Ile Ile Arg Arg Tyr
        105                 110                 115

Thr Tyr Asn Lys Ala Thr Asp Thr Leu Glu Lys Pro Val Asp Leu Leu
120                 125                 130                 135

Ala Gly Leu Pro Ser Ser Lys Asp His Gln Ser Gly Arg Leu Val Ile
                140                 145                 150

Gly Pro Asp Gln Lys Ile Tyr Tyr Thr Ile Gly Asp Gln Gly Pro Asn
                155                 160                 165

Arg Asn

<210> SEQ ID NO 29
<211> LENGTH: 36
<212> TYPE: DNA
<213> ORGANISM: Artificial
<220> FEATURE:
<223> OTHER INFORMATION: Synthetic PCR-primer
<220> FEATURE:
<221> NAME/KEY: misc_feature
<222> LOCATION: (13)..(24)
<223> OTHER INFORMATION: n corresponds to a, c, g, or t; k corresponds
      to g or t

<400> SEQUENCE: 29
cgacgtaacc agnnknnknn knnkctggct tacctg                          36

<210> SEQ ID NO 30
<211> LENGTH: 38
<212> TYPE: DNA
<213> ORGANISM: Artificial
<220> FEATURE:
<223> OTHER INFORMATION: Synthetic PCR-primer

<400> SEQUENCE: 30
gtgtgctgtg cctggttcgg caggaacagg taagccag                        38

<210> SEQ ID NO 31
<211> LENGTH: 29
<212> TYPE: DNA
<213> ORGANISM: Artificial
```

```
<220> FEATURE:
<223> OTHER INFORMATION: Synthetic PCR-primer

<400> SEQUENCE: 31
cctacctacg actcttccga cgtaaccag                                            29

<210> SEQ ID NO 32
<211> LENGTH: 30
<212> TYPE: DNA
<213> ORGANISM: Artificial
<220> FEATURE:
<223> OTHER INFORMATION: Synthetic PCR-primer

<400> SEQUENCE: 32
ccatgctctt cagtcggagt gtgctgtgcc                                           30

<210> SEQ ID NO 33
<211> LENGTH: 64
<212> TYPE: DNA
<213> ORGANISM: Artificial
<220> FEATURE:
<223> OTHER INFORMATION: Synthetic insertion fragment with four
      randomized positions
<220> FEATURE:
<221> NAME/KEY: misc_feature
<222> LOCATION: (12)..(23)
<223> OTHER INFORMATION: n is a, c, g, or t

<400> SEQUENCE: 33
gacgtaacca gnnnnnnnnn nnnctggctt acctgttcct gccgaaccag gcacagcaca         60
ctcc                                                                      64

<210> SEQ ID NO 34
<211> LENGTH: 22
<212> TYPE: DNA
<213> ORGANISM: Artificial
<220> FEATURE:
<223> OTHER INFORMATION: Synthetic sequencing primer

<400> SEQUENCE: 34
caccgttaaa gcttggatta tc                                                   22

<210> SEQ ID NO 35
<211> LENGTH: 21
<212> TYPE: DNA
<213> ORGANISM: Artificial
<220> FEATURE:
<223> OTHER INFORMATION: Synthetic sequencing primer

<400> SEQUENCE: 35
ccttcatcga aagaccatca g                                                    21
```